United States Patent
Dannhardt et al.

(10) Patent No.: US 7,485,742 B2
(45) Date of Patent: Feb. 3, 2009

(54) NON-GLYCOSIDIC AND NON-PEPTIDIC INHIBITORS OF SELECTIN, AND THE USE THEREOF

(75) Inventors: Gerd Dannhardt, Mainz (DE); Holger Ulbrich, Mainz (DE); Philip Prech, Mainz (DE); Andreas Luxenburger, Saarlouis (DE)

(73) Assignee: Johannes Gutenberg-Universität Mainz, Mainz (DE)

( * ) Notice: Subject to any disclaimer, the term of this patent is extended or adjusted under 35 U.S.C. 154(b) by 16 days.

(21) Appl. No.: 11/572,214

(22) PCT Filed: Jul. 26, 2005

(86) PCT No.: PCT/EP2005/008125
§ 371 (c)(1),
(2), (4) Date: Jul. 6, 2007

(87) PCT Pub. No.: WO2006/010598
PCT Pub. Date: Feb. 2, 2006

(65) Prior Publication Data
US 2007/0276036 A1   Nov. 29, 2007

(30) Foreign Application Priority Data
Jul. 26, 2004  (DE)  ......... 10 2004 036 213

(51) Int. Cl.
*C07C 205/00* (2006.01)
*C07C 229/00* (2006.01)
*C07C 249/00* (2006.01)

(52) U.S. Cl. .............. 560/45; 560/21; 560/43; 560/44; 562/433; 562/440; 562/442; 562/443; 562/453

(58) Field of Classification Search ............ None
See application file for complete search history.

(56) References Cited

FOREIGN PATENT DOCUMENTS

| EP | 0 671 407 A | 9/1995 |
| JP | 11 140038 A | 5/1999 |

OTHER PUBLICATIONS

Helvetica Chimica Acta (1987), 70(1), 153-7.*
Ulbrich, Holger, Einar E. Eriksson and Lennart Lindbom "Leukocyte and endothelial cell adhesion molecules as targets for therapeutic interventions in inflammatory disease" *Trends in Pharmacological Sciences*, Dec. 2003, vol. 24(12):640-647.
Wong, Chi-Huey et al., "Small Molecules as Structural and Functional Mimics of Sialyl Lewis X Tetrasaccharide in Selectin Inhibition: A Remarkable Enhancement of Inhibition by Additional Negative Charge and/or Hydrophobic Group" *J. Am. Chem. Soc.*, 1997, vol. 119:8152-8158.

* cited by examiner

*Primary Examiner*—Karl J Puttlitz
(74) *Attorney, Agent, or Firm*—Saliwanchik, Lloyd & Saliwanchik

(57) ABSTRACT

A new class of non-glycosidic and non-peptidic inhibitors of selectins with low molecular weight according to the general formula 1

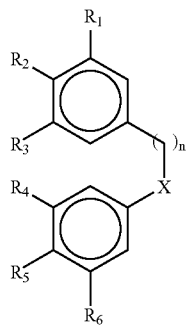

(1)

is described, as well as methods for their production. These compounds represent a new class of non-toxic, in vivo anti-inflammatory effective inhibitors of selectins, and do not exhibit the disadvantages of the glycosidic inhibitor complexes, and are furthermore more potent in vitro, compared to the known drug bimosiamose. Furthermore, medicaments containing the compounds and their uses in the treatment of diseases are described.

15 Claims, 4 Drawing Sheets

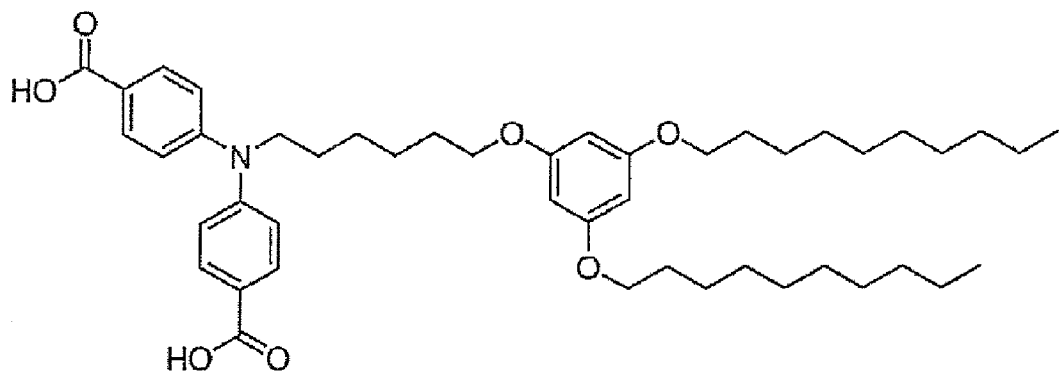

| | |
|---|---|
| Designation: | T21 |
| Systematic Name: | 4-(N-(6-(3,5-bis(decyloxy)phenoxy)hexyl)-N-(4-carboxyl-phenyl)amino)benzoic acid |
| Empiric formula: | $C_{46}H_{67}NO_7$ |
| Molecular weight: | 746,03 |
| Yield: | 86 mg (72% of theory) |
| Appearance: | colourless solid |
| IR: | KBr, $[cm^{-1}]$ = 2990, 2920, 1657, 1571, 1495, 1445, 1397, 1302, 1270, 1153, 1050, 835, 802, 760 |
| MS: | FD: 745.9 ($M^+$) |
| $^1$H-NMR: | $CDCl_3$, 300 MHz, ffi [ppm] = 8.04 (d, J = 8.74 Hz, 4H), 7.11 (d, J = 8.81 Hz, 4H), 6.08 6.03 (m, 3H), 3.92 – 3.79 (m, 8H, 3 X Ar-O-CH2, N-CH2), 1.79 – 1.70 (m, 6H, Ar-O-CH2-C$\underline{H}_2$), 1.47 – 1.26 (m, 34H, -CH2-), 0.88 (t, J = 6.65 Hz, 6H, 2 X -CH3) |
| $^{13}$C-NMR: | $CDCl_3$, 75 MHz, ffi [ppm] = 171.3 (COOH), 160.3 (3 x C-O), 151.5 ( 2 x C-N), 131.9 (4 CH), 122.3 (2 $\underline{C}$-COOH), 120.2 (4CH), 93.76 (3 CH), 68.0 (3 x CH2-O), 52.3 (CH2-N), 31.9 (2 CH2), 29.6 (11 CH2), 26.1 (3 CH2), 22.7 (2 CH2), 14.1 (2 CH3) |
| EA: | Calc. C 74.06% H 9.05% N 1.88%<br>Found C 73.50% H 9.69% N 1.70% |

FIG. 4

NON-GLYCOSIDIC AND NON-PEPTIDIC INHIBITORS OF SELECTIN, AND THE USE THEREOF

CROSS-REFERENCE TO A RELATED APPLICATION

This application is a National Stage Application of International Application Number PCT/EP2005/008125, filed Jul. 26, 2005; which claims priority to German Application No. 10 2004 036 213.0, filed Jul. 26, 2004.

DESCRIPTION

The present invention relates to a new class of non-glycosidic and non-peptidic inhibitors of selectin with low molecular weight. The invention furthermore relates to a method for producing said compounds, medicaments containing these, and their use in the treatment of diseases.

BACKGROUND OF THE INVENTION

Selectins are carbohydrate-binding adhesion molecules that, during the process of an immune defense, contribute to an increased adhesion of leukocytes to the vessel endothelium of the inflamed tissue. They are divided into L-(leukocytes), E-(endothelium) and P-(platelets and endothelium) selectin, in accordance with their cells of origin. They initiate the adhesion of leukocytes through their protein structure and their specific molecular binding properties; following a transitional binding of the corresponding ligand, the leukocytes of the flowing blood stream experience a "rolling slowing down" along the wall of the vessel. Subsequently, other adhesion molecules mediate the tight binding of the leukocytes to the endothelium as well as their extravasation, in order to complete their defensive function.

Shortly after their discovery and structural elucidation at the beginning of the 90ties, the selectins became attractive target structures for pharmaceutical research. In addition to their physiological function in the immunological events, also a dysregulation of the expression of selectin during pathological processes, such as rheumatoid arthritis, asthma, diabetes mellitus and ischemia/reperfusion, and a participation in the tissue invasion of metastatic cancer cells was observed. This motivated an intensive search for selectin-inhibiting substances.

Selectin-Ligands

For the selectins as described, only a few high-affinity ligands are known. In principle, these represent mucin-like structures, that is, long-stretched glycoproteins, to which many carbohydrate-side chains are glycosidically bound to the serine- or threonine-rich protein matrix thereof as the actual binding epitopes. Through a rapid formation and dissociation of the receptor binding to the highly flexible ligand, the rolling of the cells is mediated in the shearing flow of the vessels. The carbohydrate-epitopes that are essential for the binding are N-acetyllactosamine-based oligosaccharides in specific linkage with fucose and a terminal sialic acid (N-acetyl-neuraminic acid). The tetrasaccharide sialyl Lewis X (sLeX) is of particular importance as a binding epitope.

Although all selectins bind sLeX with only very low affinity (about 1 mM), yet, no carbohydrates having an improved binding have been found, therefore, the high binding affinity to the natural mucin ligands (about 100 nM) can not be structurally explained. Against this background, sLeX was used as a standard ligand for structure-effect-relationships, in order to characterize the binding properties as well as for the search for selectin-inhibitors.

Modification of the Lead Structure Sialyl Lewis X

Due to the fact that the tetrasaccharide sialyl Lewis X (sLeX) is able to bind to all three selecting, it functions as central lead substance for the search for selectin inhibiting compounds. Based on the x-ray structural data of the E-selectin (Graves, B. J., et al., Insight into E-selectin/ligand interaction from the crystal structure and mutagenesis of the lec/EGF domains. Nature 367 (1994) 532-538.), and several NMR-examinations of the dissolved sLeX, or sLeX bound to E-selectin (Cooke, R. M., et al. The conformation of the sialyl Lewis x ligand changes upon binding to E-Selectin. *Biochemistry* 33 (1994) 10591-10596; Kogan, T. P., et al., A single amino acid residue can determine the ligand specificity of E-Selectin. *J. Biol. Chem.* 270 (1995) 14047-14055.), the structural elements that are essential for the binding of the lectin domain could be identified: the negative charge of the sialic acid, the 2-, 3-, and 4-positioned hydroxy group of the fucose, as well as the 6-positioned hydroxy group of the galactose. Introducing structural modifications while maintaining the structural features as just mentioned, it was tried to obtain selectin inhibitors that exhibit an improved binding. The disadvantages of glycosidic inhibitors are the complex synthesis pathway, the high costs of the starting compounds, the difficult structural elucidation, the hydrolytic instability, and the relatively low binding affinity. For an extensive review of synthetic selectin inhibitors, reference shall be made to Simanek et al. (Simanek, E. E., et al., Selectin-carbohydrate interactions: From natural ligands to designed mimetics. *Chem. Rev.* 98 (1998) 833-862.).

The simplest synthetic modification of the sLeX consists in a replacement of the negatively charged sialic acid through simpler negatively charged structural elements. Thus, sulfur-, phosphor-, and carboxylic acid-derivatives at the C3 of the galactose have been described. These structural variations resulted in similar binding affinities such as the one for sLeX itself (Ohmoto, H., et al., Studies on selectin blockers 1: Structure activity relationships of Sialyl Lewis x analogs. *J. Med. Chem.* 39 (1996) 1339-1343.).

A further simplification consists in the substitution of the N-acetylated glucose that does not contribute to the binding, but is merely responsible for the optimal orientation of the overall structure. The substitution of the glucose by alkanedioles or cyclohexanedioles without or with simultaneous substitution of the sialic acid led to derivatives that, in some cases, also exceeded the effectivity of sLeX (Norman, K. E., et al., Sialyl Lewis X (sLex) and an sLex mimetic, CGP69669A, disrupt E-selectin-dependent leukocyte rolling in vivo. *Blood* 91 (1998) 475-483.). The simultaneous substitution of glucose and galactose gave rigid and stabile fucose-sialic acid-derivatives, which, due to the lack of the galactose-6-hydroxy group, nevertheless, gave no improved effect.

The largest group by number of the sLeX-analogs as tested consists of monosaccharide-compounds, wherein, while maintaining the fucose, the other essential binding epitopes in the molecule were replaced by non-glycosidic structures. Most successful are molecules, wherein specific peptides at the fucose simulate the contribution to the binding of the galactose and the negative sialic acid. Some substances exhibit a similar, in individual cases even a markedly enhanced binding affinity to the selectins, compared with the sLeX (Wong, C. H., et al., Small molecules as structural and functional mimics of sLex tetrasaccharide in selectin inhibition: A remarkable enhancement of inhibition by additional negative charge and for hydrophobic groups. *J. Am. Chem. Soc.* 119 (1997) 8152-8158.). Starting from sLeX, additional binding epitopes were searched for. It was found through the derivatization of the sLeX, and the computer simulation of the binding at the lectin domain, that a hydrophobic substitution at the glycosidic hydroxy group or at the amine of the glucosamine drastically improved the binding properties. New derivatives with aromatic ring systems at the amine or branched chain fatty acids at the glycosidic residue of the glucosamines, but also simplified sLeX-analogs with fatty acid substitutions were successfully tested (Ramphal, J. Y., et al., Ligand interactions with E-Selectin. Identification of a new site for recognition of N-Acyl Aromatic Glucosamine substituents of Sialyl Lewis x. *J. Med. Chem.* 39 (1996) 1357-1360.), and partially exhibited a more than 10-fold stronger binding, when compared with sLeX.

Another theory related to the enhancement of the binding is based on the joint cooperation of several singular bonds. This multi-valence hypothesis is also discussed as the underlying and effective principle of the natural selectin ligands. Based on this, several oligo- and polymeric derivatives were synthesized, wherein sLeX-molecules (Renkonen, O., et al., Synthesis of new nanomolar saccharide inhibitors of lymphocyte adhesion: Different polylactosamine backbones present multiple Sialyl Lewis X determinants to L-Selectin in high affinity mode. *Glycobiology* 7 (1997) 453-461.), or their structurally simplified glycosides (Manning, D. D., et al., Neoglycopolymer inhibitors of the selecting. *Tetrahedron* 53 (1997) 11937-11952.), are sterically tightly connected through carrier molecules. Despite the partially improved binding parameters, the multi-valence hypothesis is differently discussed. Binding studies using a multimeric, non-covalently fixed sLeX-array in liposomes (Stahn, R., et al., Multivalent sLex ligands of definite structure as inhibitors of E-selectin mediated cell adhesion. *Glycobiology* 8 (1998) 311-319) or in planar model membranes (Vogel, J., et al., The role of glycolipids in mediating cell adhesion: A flow chamber study. *Biochim. Biophys. Acta* 1372 (1998) 205-215.), support the hypothesis.

Aggravating for a valuing comparison of all selectin inhibitors as synthesized is the fact that different test systems are used in the individual research groups.

Until now, only one selectin inhibiting substance having a glycosidic structure can be found in clinical trials (phase IIa), namely the pan-selectin antagonist bimosiamose (1,6-bis[3-(3-carboxymethylphenyl)-4-(2-alpha-D-mannopyranosyloxy)phenyl]hexane), which exhibits an essentially higher affinity to the selectins compared to sLeX. The Revotar AG is testing bimosiamose for the treatment of psoriasis and atopic dermatitis (Ulbrich H, et al. Leukocyte and endothelial cell adhesion molecules as targets for therapeutic interventions in inflammatory disease. *Trends Pharmacol Sci.* (2003) 640-647.).

It is therefore an object of the present invention to provide inhibitors of selectin which overcome the disadvantages of inhibitors of selectin that are known in the state of the art, and which, in addition are more stable and synthetically more accessible.

According to the invention, this object is solved by providing compounds of the general formula 1

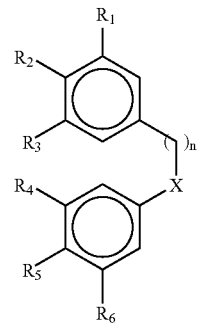

wherein
n is 0 or 1,
$R_1$ to $R_6$ independently are H, COOH, COOCH$_3$, COOC$_2$H$_5$ or halogen, and
X is C=N—O—(CH$_2$)$_m$—Y or N—C(=O)—(CH$_2$)$_m$—Y,
wherein
m is 5 or 6, and
Y is

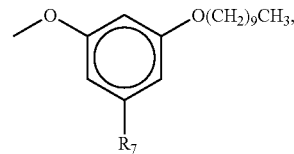

wherein
$R_7$ is H or O(CH$_2$)$_9$CH$_3$, or derivatives thereof, their diastereomers, and pharmaceutically acceptable salts of said compounds.

Thereby, preferred are compounds, that are derived from formula 2, wherein formula 2 is

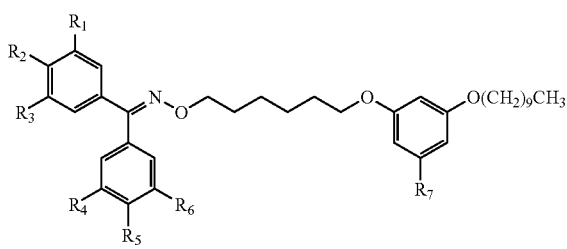

wherein
$R_1$ is H,
$R_2$ is H, COOH, COOCH$_3$ or halogen,
$R_3$ is H, COOH or COOCH$_3$,
$R_4$ is H,
$R_5$ is H, COOH, COOCH$_3$ or halogen,
$R_6$ is H, and
$R_7$ is H or O(CH$_2$)$_9$CH$_3$, or derivatives thereof, their diastereomers, and pharmaceutically acceptable salts of said compounds.

Furthermore preferred are compounds, that are derived from formula 3, wherein formula 3 is

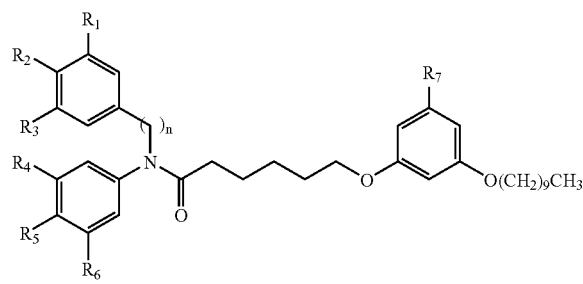

(3)

wherein
n is 0 or 1,
$R_1$ is H, COOH or COOCH$_3$,
$R_2$ is H, COOH, COOCH$_3$ or COOC$_2$H$_5$,
$R_3$ is H, COOH or COOCH$_3$,
$R_4$ is H, COOH or COOCH$_3$,
$R_5$ is H, COOH, COOCH$_3$ or COOC$_2$H$_5$,
$R_6$ is H, and
$R_7$ is H or O(CH$_2$)$_9$CH$_3$, or derivatives thereof, their diastereomers, and pharmaceutically acceptable salts of these compounds.

A preferred embodiment of the present invention is represented by pharmaceutical compositions that comprise at least one compound according to the formulae 1-3, and suitable additives or auxiliary agents. Such suitable additives and auxiliary agents are known to the person of skill and from the state of the art.

In these pharmaceutical compositions, the compounds can be present in form of a depot substance or as a precursor, together with a suitable, pharmaceutically acceptable diluent or carrier substance.

It is preferred that the compounds are present in a pharmaceutical composition in an amount of 0.1 to 1000 mg, more preferred of 1 to 100 mg per dosage unit.

Furthermore, additional selectin inhibitors can be contained in the pharmaceutical compositions. These additional selectin inhibitors can comprise usual selectin inhibitors that are known to the person of skill, such as, for example, sialyl Lewis X (sLeX), a large number of sLeX-analogs, such as, for example, monosaccharide and oligosaccharide-compounds, and glycosidic selectin inhibitors, such as, for example, bimosiamose. Synthetic selectin inhibitors can be used (for this, see also: Simanek, E. E., et al., Selectin-carbohydrate interactions: From natural ligands to designed mimetics. *Chem. Rev.* 98 (1998) 833-862.).

Preferred forms of the pharmaceutical compositions are tablets, dragees, capsules, droplets, suppositories, preparations for injection or infusion for peroral, rectal or parenteral use. Such administration forms and their production are known to the person of skill.

It is preferred that the compounds are present in a pharmaceutical composition in such an amount that an amount in a concentration range of between 0.1 and 100 μM can be found during a treatment in vivo.

The method according to the invention for the synthesis of a compound according to the formulae 1 to 3 preferably comprises the synthesis from 1-(6-bromohexyloxy)-3,5-didecyloxybenzene and a compound selected from the group of bis(4-methoxycarbonylphenyl)methanone, N N-bis(4-methoxycarbonylphenyl)amine, and N-(4-carboxybenzyl)-N-(4-carboxyphenyl)amine.

In doing so, it is preferred that a compound according to formula 2 is synthesized from bis(4-methoxycarbonylphenyl)methanone (compound 6 in scheme 1) and 1-(6-bromohexyloxy)-3,5-didecyloxybenzene (compound 10 in scheme 1).

It is furthermore preferred that the production of a compound according to formula 3 comprises the synthesis from N,N-bis(4-methoxycarbonylphenyl)amine (compound 15 a in scheme 2) or N-(4-carboxybenzyl)-N-(4-carboxyphenyl)amine (compound 15 b in scheme 2) and 1-(6-bromohexyloxy)-3,5-didecyloxybenzene (compound 10 in scheme 1).

Preferably, a synthesis of the compounds according to the invention takes place as illustrated in the schemes 1 and 2.

The present invention provides a novel class of non-glycosidic and non-peptidic selectin inhibitors with low molecular weight. These were synthesized as ligands for an inhibition of the selectin-mediated leukocyte adhesion in accordance with different strategies (schemes 1 + 2), based on a pharmacophoric model including molecular modeling methods.

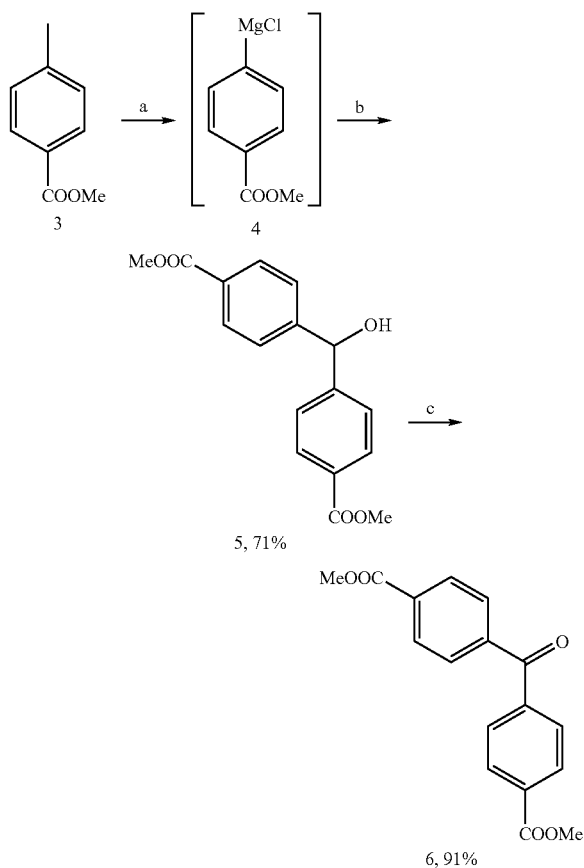

Scheme 1

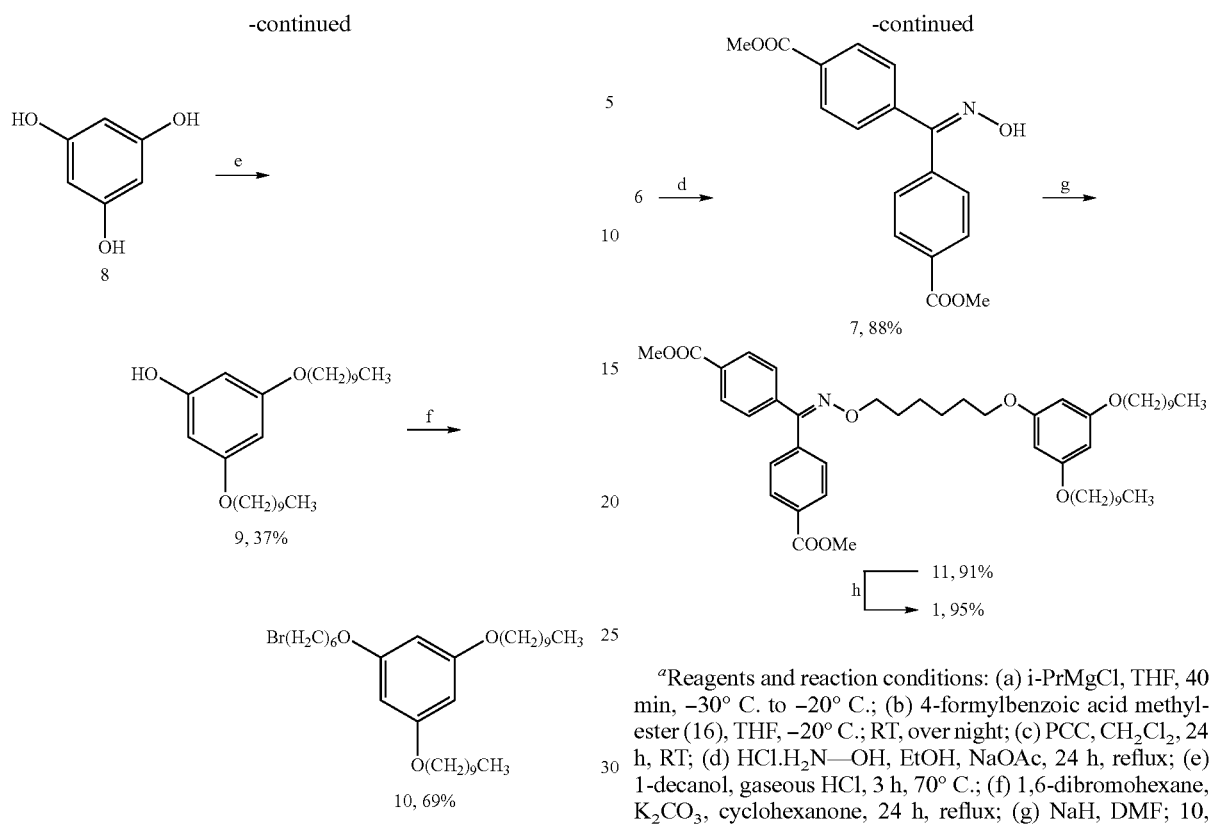
<sup>a</sup>Reagents and reaction conditions: (a) i-PrMgCl, THF, 40 min, −30° C. to −20° C.; (b) 4-formylbenzoic acid methyl-ester (16), THF, −20° C.; RT, over night; (c) PCC, CH$_2$Cl$_2$, 24 h, RT; (d) HCl.H$_2$N—OH, EtOH, NaOAc, 24 h, reflux; (e) 1-decanol, gaseous HCl, 3 h, 70° C.; (f) 1,6-dibromohexane, K$_2$CO$_3$, cyclohexanone, 24 h, reflux; (g) NaH, DMF; 10, n-BU4NI, 2 h, RT; (h) 0.5 M NaOH, EtOH/THF, 24 h, RT; (see example 8).
Scheme 2
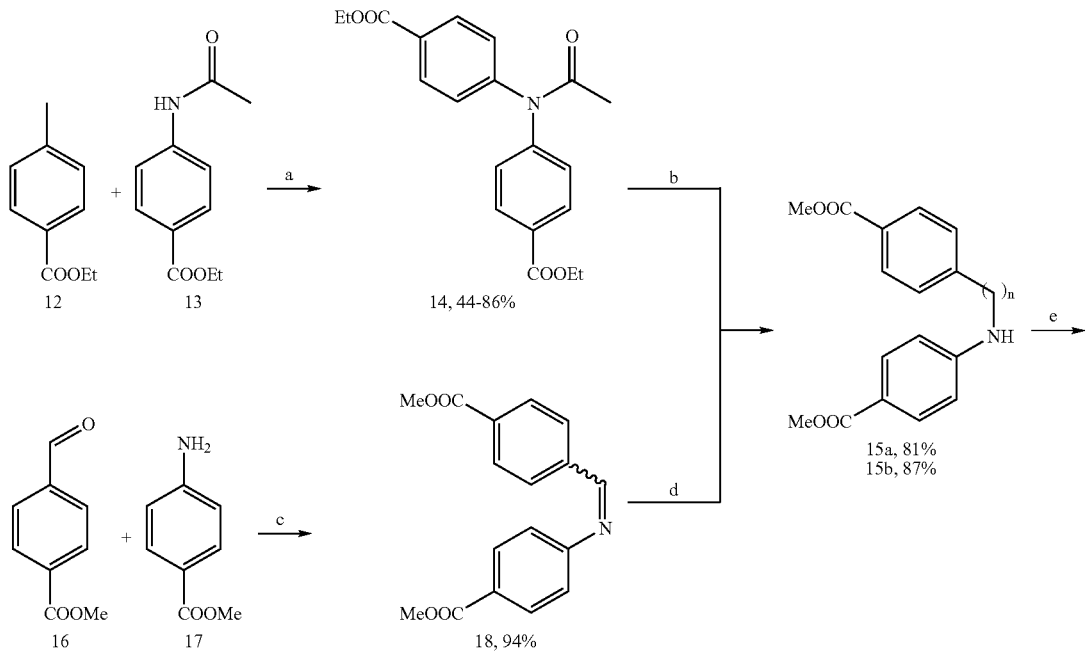

-continued

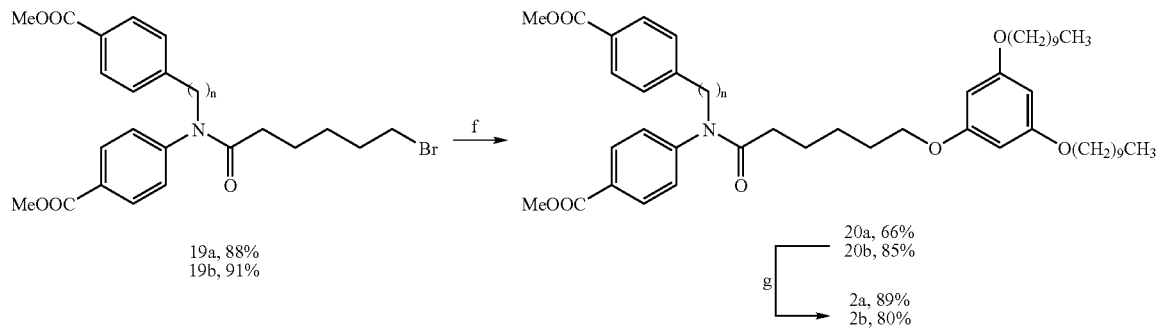

19a, 88%
19b, 91%

20a, 66%
20b, 85%

2a, 89%
2b, 80% a) n = 1, b) n = 0

$^a$Reagents and reaction conditions: (a) Cu, CuI, $K_2CO_3$, n-$Bu_2O$, 4 d, reflux; (b) $NaOCH_3$, $CH_3OH$, 1.5 h, reflux; (c) MeOH, 1 h, reflux; (d) $NaBH_4$, MeOH, 24 h, RT; (e) NaH, n-$Bu_2O$, 2 h, RT; 6-bromohexanoic acid chloride, 4 h, reflux; (f) 9, $K_2CO_3$, KI, cyclohexanone, 5 h, reflux; (g) 0.5 M LiOH, THF, 8 h, 5° C., then 16 h, 15° C.; (see example 8).

Subsequently, the compounds as produced according to the invention can be derivatized. Preferred derivatizations comprise the formation of ester-, amide-, and hydroxamic acid-derivatives of the compounds according to the invention.

Preferred members of the compounds that can be derived from the formulae 1-3 comprise the compounds that are shown in the overviews 1 and 2 for the formulae.

Overview 1 for formulae formula (2)

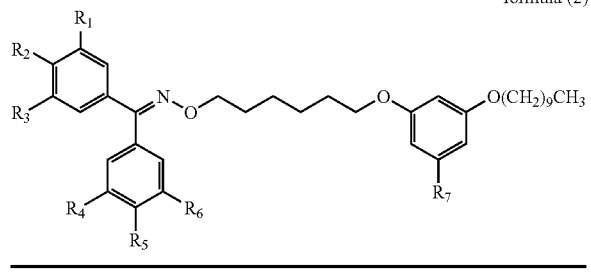

| | |
|---|---|
| T2 (syn.: 11) | $R_1$ = H |
| | $R_2$ = $COOCH_3$ |
| | $R_3$ = H |
| | $R_4$ = H |
| | $R_5$ = $COOCH_3$ |
| | $R_6$ = H |
| | $R_7$ = $O(CH_2)_9CH_3$ |
| T4 (syn.: 1) | $R_1$ = H |
| | $R_2$ = COOH |
| | $R_3$ = H |
| | $R_4$ = H |
| | $R_5$ = COOH |
| | $R_6$ = H |
| | $R_7$ = $O(CH_2)_9CH_3$ |
| T8 | $R_1$ = H |
| | $R_2$ = H |
| | $R_3$ = COOH |
| | $R_4$ = H |
| | $R_5$ = COOH |
| | $R_6$ = H |

Overview 1 for formulae formula (2)

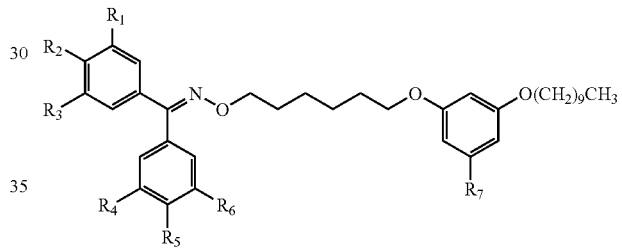

| | |
|---|---|
| | $R_7$ = $O(CH_2)_9CH_3$ |
| T9 | $R_1$ = H |
| | $R_2$ = H |
| | $R_3$ = $COOCH_3$ |
| | $R_4$ = H |
| | $R_5$ = $COOCH_3$ |
| | $R_6$ = H |
| | $R_7$ = $O(CH_2)_9CH_3$ |
| T10 | $R_1$ = H |
| | $R_2$ = Cl |
| | $R_3$ = H |
| | $R_4$ = H |
| | $R_5$ = Cl |
| | $R_6$ = H |
| | $R_7$ = $O(CH_2)_9CH_3$ |
| T27 | $R_1$ = H |
| | $R_2$ = COOH |
| | $R_3$ = H |
| | $R_4$ = H |
| | $R_5$ = COOH |
| | $R_6$ = H |
| | $R_7$ = H |

Overview 2 for formulae

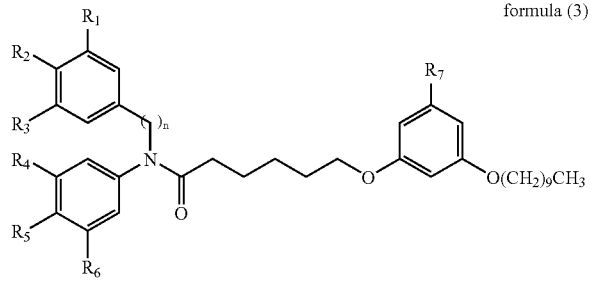

formula (3)

| | |
|---|---|
| T1 | n = 0<br>$R_1$ = H<br>$R_2$ = COOC$_2$H$_5$<br>$R_3$ = H<br>$R_4$ = H<br>$R_5$ = COOC$_2$H$_5$<br>$R_6$ = H<br>$R_7$ = O(CH$_2$)$_9$CH$_3$ |
| T3 (syn.: 2a) | n = 0<br>$R_1$ = H<br>$R_2$ = COOH<br>$R_3$ = H<br>$R_4$ = H<br>$R_5$ = COOH<br>$R_6$ = H<br>$R_7$ = O(CH$_2$)$_9$CH$_3$ |
| T5 (syn.: 20a) | n = 0<br>$R_1$ = H<br>$R_2$ = COOCH$_3$<br>$R_3$ = H<br>$R_4$ = H<br>$R_5$ = COOCH$_3$<br>$R_6$ = H<br>$R_7$ = O(CH$_2$)$_9$CH$_3$ |
| T6 | n = 0<br>$R_1$ = H<br>$R_2$ = H<br>$R_3$ = COOCH$_3$<br>$R_4$ = H<br>$R_5$ = COOCH$_3$<br>$R_6$ = H<br>$R_7$ = O(CH$_2$)$_9$CH$_3$ |
| T7 | n = 0<br>$R_1$ = H<br>$R_2$ = H<br>$R_3$ = COOH<br>$R_4$ = H<br>$R_5$ = COOH<br>$R_6$ = H<br>$R_7$ = O(CH$_2$)$_9$CH$_3$ |
| T17 (syn.: 2b) | n = 1<br>$R_1$ = H<br>$R_2$ = COOH<br>$R_3$ = H<br>$R_4$ = H<br>$R_5$ = COOH<br>$R_6$ = H<br>$R_7$ = O(CH$_2$)$_9$CH$_3$ |
| T18 (syn.: 20b) | n = 1<br>$R_1$ = H<br>$R_2$ = COOCH$_3$<br>$R_3$ = H<br>$R_4$ = H<br>$R_5$ = COOCH$_3$<br>$R_6$ = H<br>$R_7$ = O(CH$_2$)$_9$CH$_3$ |
| T20 | n = 1<br>$R_1$ = COOH<br>$R_2$ = H<br>$R_3$ = H<br>$R_4$ = H<br>$R_5$ = COOH<br>$R_6$ = H |
| T22 | $R_7$ = O(CH$_2$)$_9$CH$_3$<br>n = 1<br>$R_1$ = H<br>$R_2$ = COOCH$_3$<br>$R_3$ = H<br>$R_4$ = H<br>$R_5$ = COOCH$_3$<br>$R_6$ = H<br>$R_7$ = H |
| T23 | n = 0<br>$R_1$ = H<br>$R_2$ = COOH<br>$R_3$ = H<br>$R_4$ = COOH<br>$R_5$ = COOH<br>$R_6$ = H<br>$R_7$ = O(CH$_2$)$_9$CH$_3$ |
| T24 | n = 1<br>$R_1$ = COOCH$_3$<br>$R_2$ = H<br>$R_3$ = H<br>$R_4$ = H<br>$R_5$ = COOCH$_3$<br>$R_6$ = H<br>$R_7$ = H |
| T25 | n = 0<br>$R_1$ = H<br>$R_2$ = COOCH$_3$<br>$R_3$ = H<br>$R_4$ = COOCH$_3$<br>$R_5$ = COOCH$_3$<br>$R_6$ = H<br>$R_7$ = O(CH$_2$)$_9$CH$_3$ |
| T26 | n = 1<br>$R_1$ = COOH<br>$R_2$ = H<br>$R_3$ = H<br>$R_4$ = H<br>$R_5$ = COOH<br>$R_6$ = H<br>$R_7$ = H |
| T28 | n = 1<br>$R_1$ = H<br>$R_2$ = COOH<br>$R_3$ = H<br>$R_4$ = H<br>$R_5$ = COOH<br>$R_6$ = H<br>$R_7$ = H |

T21:

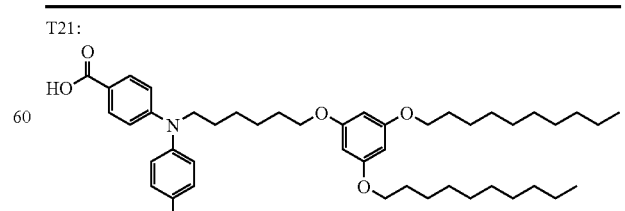

4-(N-(6-(3,5-bis(decyloxy)phenoxy)hexyl)-N-(4-carboxyl-phenyl)amino) benzoic acid; C$_{46}$H$_{67}$NO$_7$ (T21)

Said 4-[(N-4-carboxyphenyl-N-acyl)amino]benzoic acid-derivatives or 4-[(N-4-carboxyphenyl-N-acyl)imino]benzoic acid-derivatives, respectively, as mimetics of sLeX, have an essentially higher affinity (f≈6 in the static assay, see example 1) for the selecting, compared to the above-mentioned bimosiamose itself. These mimetics contain functional groups, such as, for example, hydroxy groups and acidic units, in order to mimic fucose and sialic acid, aromatic regions as substitutions for lactosamine, having a defined distance from lipophilic and hydrophilic structural elements.

The results of a static leukocyte-adhesion-assay using compounds T1 to T27 according to the invention (see FIG. 1 as well as example 1) clearly show that the most potent of the compounds according to the invention are carboxylic acids. Thus, different carboxylic acids, each having an amide-, oxime-, and amino-structural element, respectively, were produced and tested. With the exception of T25, all esters only exhibited a weak effect on the reduction of the adhesion. As a comparison: bimosiamose, in a concentration of 600 µM, has about the same potency as T3 in a concentration von 100 µM.

In addition, in a mouse-peritonitis-model, a model of acute inflammation, it could be exemplary shown that the substances according to the invention led to a reduction of the infiltration of polymorphonuclear leukocytes (PMNs) into the peritoneum (see FIG. 2 and example 7), and thus are anti-inflammatory effective.

Furthermore, in toxicity-assays those structural elements were already identified that could be responsible for a cytotoxicity of the compounds according to the invention (see FIG. 3 and example 6).

The compounds according to the invention that can be derived from the formulae 1 to 3 can be used as medicaments.

In doing so, preferred is the use for the treatment of diseases, wherein the selectin-mediated leukocyte adhesion is dysregulated.

Furthermore preferred is the use for the treatment of inflammatory diseases. The inflammatory diseases that can be treated according to the invention comprise peritonitis and rheumatoid arthritis. Furthermore, the treatment of tumorous diseases is possible.

The compounds according to the invention are preferably used as inhibitors of selectin and for an inhibition of the selectin-mediated leukocyte adhesion.

In summary, it can be said that the present invention comprises a novel class of non-toxic, in vivo anti-inflammatory effective, non-glycosidic and non-peptidic inhibitors of selectin that do not exhibit the disadvantages of the glycosidic inhibitor complexes, such as 1. the complex synthesis pathway, 2. the high costs of the starting compounds 3. the laborious elucidation of the structure, 4. the hydrolytic instability, and 5. the relatively low binding affinity, and that are furthermore more potent in vitro than the drug bimosiamose which is currently in the clinical phase II.

In the context of the present invention, a "derivative" shall mean a compound, which is derived from one of the general formulae 1, 2 or 3 that, for example, is substituted with several of the residual groups as given above for $R_1$ to $R_6$ and X or Y, as well as mixtures of several of these compounds, which, for example, can be processed into a "personalized" medicament which is adjusted to with respect to the respective disease to be treated and/or the patient on the basis of diagnostic data, or data with respect to the success or progression of the treatment. A derivative shall also include a compound that can be produced in accordance with a synthesis pathway that is different from the one that is (exemplary) mentioned herein.

Preferred derivatizations comprise the formation of ester-, amide- and hydroxamic acid-derivatives of the compounds according to the invention.

In the context of the present invention, a "precursor" of a substance shall first mean a substance that, during the administration for the treatment, is modified by the conditions inside the body (e.g. pH in the stomach, or the like) in such a manner, or, after uptake into the body, is metabolized in such a manner that the compounds according to the invention or their derivatives are formed as effective substances.

FIGURES AND EXAMPLES

The present invention is now further illustrated by the following examples with reference to the attached Figures, nevertheless, without being limited to these examples. In the Figures FIG. 1 shows the testing of T1-T27 in the static adhesion-assay, with

| Column | Type of structure | Type of compound | Number of chains |
|---|---|---|---|
| 1 | Amide | Ester | 2 |
| 2 | Oxime | Ester | 2 |
| 3 | Amide | Carboxylic acid | 2 |
| 4 | Oxime | Carboxylic acid | 2 |
| 5 | Amide | Ester | 2 |
| 6 | Amide | Carboxylic acid | 2 |
| 7 | Oxime | Carboxylic acid | 2 |
| 8 | Oxime | Ester | 2 |
| 9 | Oxime | Chlorine-compound | 2 |
| 10 | Amide | Carboxylic acid | 2 |
| 11 | Amide | Ester | 2 |
| 12 | Amide | Carboxylic acid | 2 |
| 13 | Amine | Carboxylic acid | 2 |
| 14 | Amide | Ester | 1 |
| 15 | Amide | Carboxylic acid | 2 |
| 16 | Amide | Ester | 1 |
| 17 | Amide | Ester | 2 |
| 18 | Amide | Carboxylic acid | 1 |
| 19 | Oxime | Carboxylic acid | 1 |
| 20 | Control | | |
| 21 | Control | | |
| 22 | Control | | |

The reduction of adhesion of adhering leukocytes to the monolayer stimulated with TNF-α was set to 0%, the one in the untreated control-wells was set to 100%.

FIG. 3 shows the results of the XTT-viability test versus MM6-cells for an examination of the cytotoxic behavior of compounds having different structural elements, with

| Column | Type of structure | Type of compound | Number of chains |
|---|---|---|---|
| 1 | | Control | |
| 2 | Amide | Carboxylic acid | 2 |
| 3 | Oxime | Carboxylic acid | 2 |
| 4 | Amide | Carboxylic acid | 2 |
| 5 | Amine | Carboxylic acid | 2 |
| 6 | Amide | Ester | 1 |
| 7 | Amide | Ester | 2 |
| 8 | Amide | Carboxylic acid | 1 |

-continued

| Column | Type of structure | Type of compound | Number of chains |
|---|---|---|---|
| 9 | Oxime | Carboxylic acid | 1 |
| 10 | | Control | |

FIG. 4 shows the chemical structure of the compound T21. Also provided are the physical and spectral characteristics of the compound.

EXAMPLE 1

Static Adhesion Assay

Following seeding in 24 well-plates, the examination of the adhesion was performed using (bovine aorta endothelial cells) BAEC monolayers of the cell passage 1-3 seven days. Before performing the assay, the completeness and the uniformity of the BAEC-monolayer was microscopically ensured. The culture medium (500 ml of medium M199, to which 6 ml of penicillin/streptomycin solution 1%, 6 ml L-glutamine (200 mM) and 100 ml (20%) of fetal calf serum, Sigma, Munich, were added) was removed, and the monolayer was washed twofold with DPBS (1000 µl/well, 37° C.). Subsequent to washing, the cells were treated with the cell culture medium containing 20 ng/ml of recombinant tumor necrosis-factor-alpha (TNFα) (in the presence of the respective test substance, dissolved in dimethylsulfoxide (DMSO) or only with DMSO as vehicle) for 20 minutes at 37° C. and 5% $CO_2$ for 4 hours. After another twofold washing with DPBS (1000 µl/well, 37° C.) 900 µl of the culture medium and 100 µl of a PMN-suspension ($10^6$ cells per ml) were added per well, and incubated for 30 minutes at 37° C. and 5% $CO_2$. Non-adherent cells were removed by twofold washing with DPBS (1000 µl/well, 37° C.). Culture medium (1000 µl/well, 37° C.) was added before the microscopic evaluation, $10^{-4}$-$10^{-7}$ mol/l were used as concentrations of the substances as tested. The vitality of the BAEC after the incubation with cytokines or substances as tested was confirmed with trypan-blue-exclusion and microscopic examination (see example 2 and 3).

Figure 1:
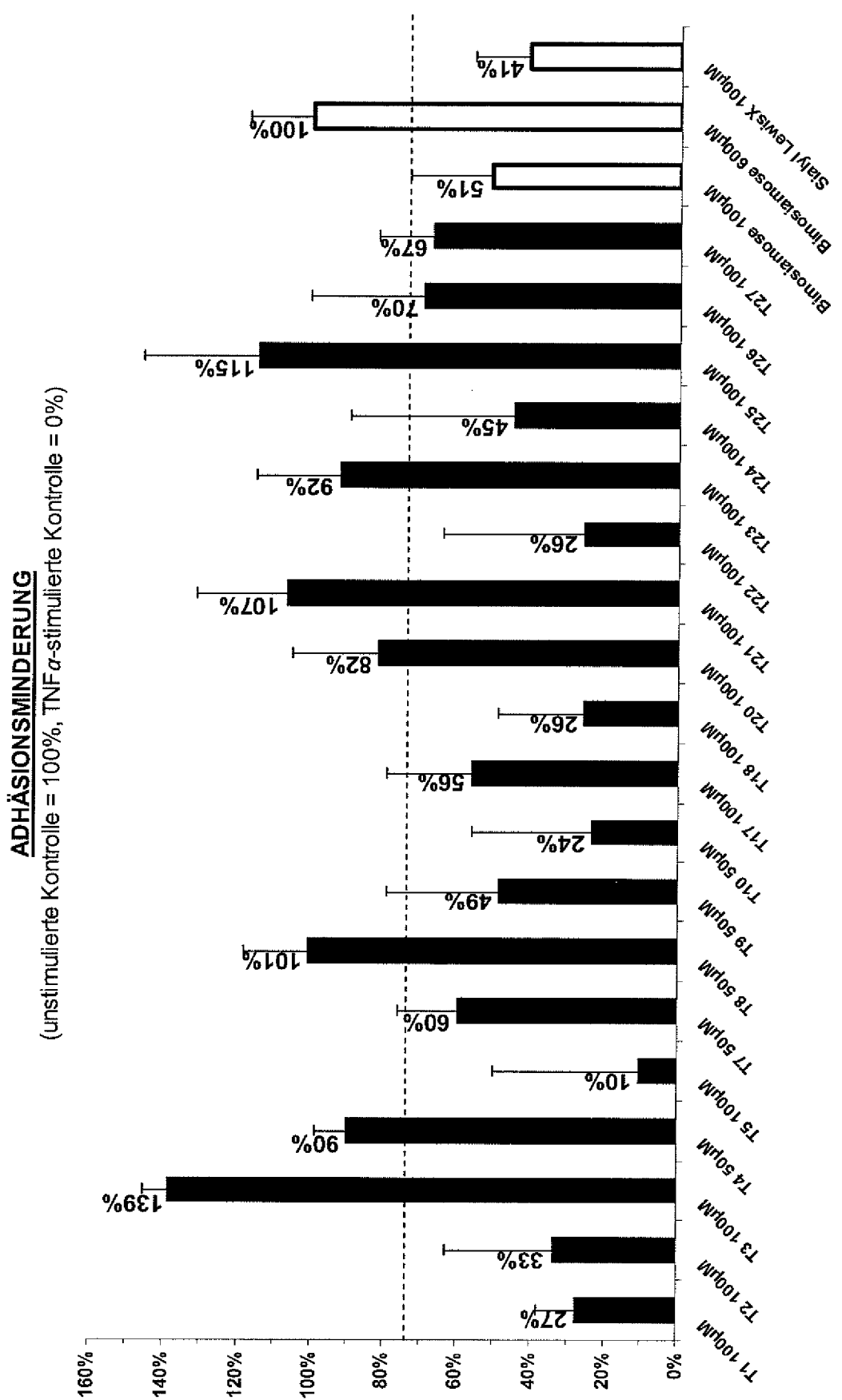

In FIG. 1, the testing of compounds T1 to T27 in the static assay is summarized (Ulbrich, H., Prech, P., Luxenburger, A. and Dannhardt, G. Characterization of a computerized assay for rapid and easy determination of leukocyte adhesion to endothelial cells. Eur. J. Phar. Sci. submitted; Dannhardt, G. and Ulbrich, H., In-vitro test system for the evaluation of cyclooxygenase-1 (COX-1) and cyclooxygenase-2 (COX-2) inhibitors based on a single HPLC run with UV detection using bovine aortic coronary endothelial cells (BAECs). Inflamm. Res. (2001) 262-269.). The reduction of the adhesion of attaching leukocytes to the monolayer stimulated with TNF-α was set to 0%, the one in the untreated control-wells was set to 100%.

FIG. 1 clearly shows that, in each case, carboxylic acids were the most potent compounds. In doing so, different carboxylic acids were produced and tested that each had an amide-, oxime-, or amino-structural element, respectively. With the exception of T25, all esters have only a weak effect on the reduction of the adhesion. For comparison: bimosiamose in a concentration of 600 µM has about the same potency as T3 in a concentration of 100 µM.

EXAMPLE 2

Visualization and Cell-Counting

The BAEC-sections were analyzed with an inverse Leica DM IRS-microscope (Leica, Bensheim, Germany) at 100-fold magnification. The analysis was performed in the centre of each monolayer, where the BAEC-layer with the adherent PMNs could be focused sharply. The pictures of the BAEC-sections were taken up with a resolution of 1200×1000 pixels using a Leica DC 200 digital camera that was connected to the microscope, and stored on a PC as bitmap (bmp) or as tagged image file format (tiff) by means of the Leica picture archive-software (Leica Mikrosysteme, Bensheim, Germany). For the manual counting of PMNs, several randomly selected sections of 0.25 $mm^2$ in size from the centre of the respective well of the well-plate were counted. The counting took place using the picture archive-software IM 1000. (Leica Mikrosysteme, Bensheim, Germany). In order to do so, each PMN in the area as chosen was counted by a PC-mouse click, and the counted cells were labeled. This manual counting was done by two blinded independent observers. The manual method of counting has a mean deviation of ±10%.

EXAMPLE 3

Analysis of Pictures

The analysis of the pictures was performed using the publicly available ImageJ-software (available at http://rsb.info.nih.gov/ij), installed on a standard-PC (Maxdata, Mergel, Germany). All pictures as obtained in a test run were grouped into an series, and then analyzed in an automated method using a specifically programmed macro. During the analysis, the colored picture was first transformed into an 8-bit picture. Subsequently, the allocation of the grey tones of each picture was plotted, the threshold of the grey tones was defined, and finally the cells were counted. In order to do so, the macro "of the customer-specific particle analysator" (authors: Roos, G., Rasband, W.; http://rsb.info.nih.gov/ij/plugins/particle-analyzer.html) was used. Counted PMNs were displayed as filled black circles. For all particles, the following parameters were recorded, area in pixels, minimum/maximum/average of the grey tones and the circularity ($4\pi \cdot (area/circumference^2)$). The borders for the area and the parameter of the circularity were adjusted to the values corresponding to the size and the form of the PMNs that were used in the experiment.

EXAMPLE 4

Flow-Through Chamber-Cell-Adhesion-Assay

Dynamic laminar flow-trough assays were performed on BAECs that were first grown to confluence in 6-well-plates in an incubator at 5% $CO_2$ and 37° C. In order to do so, the cells were incubated for 4 hours with medium (500 ml medium M199, to which 6 ml of penicillin/streptomycin solution 1%, 6 ml L-glutamine (200 mM) and 100 ml (20% ig) fetal calf serum were added) alone (control) or with medium containing 10 ng/ml TNFα/IL-1β (R&D systems) in the presence/ absence of substances as tested that had been dissolved in DMSO (10-100 μM final concentration). In another experimental series, the leukocytes were incubated for 4 hours with medium alone (control) or with medium containing 10 ng/ml TNFα/IL-1β in the presence/absence of the substances as tested that had been dissolved in DMSO (10-100 mM final concentration).

Following the incubation the endothelial cells were washed with PBS, and a flat-polished flow-through chamber (Glycotech) was attached onto the BAEC-monolayer. MM6 or PMNs ($1.0 \times 10^6$ cells/ml), suspended in RPMI medium plus 1% FCS, were perfused through the flow chamber at a constant shear stress of 1 dyne/cm² for 4 minutes. The rolling and the adhering leukocytes were visualized, and within the first minute were counted in four different areas of each well of the 6-well plate that were randomly selected. This took place using an inverse microscope that was connected to a video camera (Kappa CF 15/2) and a video recorder (Panasonic SVHSTL700). All data were analyzed with Microsoft Excel. $IC_{50}$ values were calculated with the program GRAFIT, Erithacus Software Ltd., Great Britain.

EXAMPLE 5

E-selectin P-Selectin-Cellular Adhesion-Assay

The abilities of the substances, to block the adhesion of MM6 cells to recombinant selectin-protein was measured in a "cell-selectin"-assay. Recombinant soluble P- or E-selectin-protein, respectively that were obtained from R&D (Minneapolis, Mangan), were diluted to 5.0 μg/ml in Dulbeccos PBS containing calcium and magnesium. (PBS+). In order to obtain plates coated with cell adhesion molecules (CAMs), 50 μl of each the respective human recombinant CAM (5 μg/ml; R&D Systeme, MN) was added into the centre of each hole of the 6-well plate, and incubated over night at 4° C. The plates were washed three times with 100 μl PBS+, and incubated for 60 minutes with 100 μl of a solution of the substance to be tested (or the vehicle) in RMPI (1% FCS and 1% DMSO) in different final concentrations. For the substances as tested twofold or threefold determinations were performed, respectively. Then, the plates for the cellular adhesion-assay were washed three times with 100 μl PBS+, and a flat-polished flow-through chamber (Glycotech) was attached onto the BAEC monolayer. MM6 or PMNs ($1.0 \times 10^6$ cells/ml), suspended in RPMI medium plus 1% FCS, were perfused through the flow chamber at a constant shear stress of 1 dyne/cm² for 4 minutes. The rolling and the attached leukocytes were visualized, and counted in the first minute in four different randomly selected areas of each well of the 6-well plate. This was recorder with an inverse microscope that was connected to a video camera (Kappa CF 15/2) and to a video recorder (Panasonic SVHSTL700). All data were with analyzed with Microsoft Excel. The $IC_{50}$ values were calculated with the program GRAFIT, Erithacus Software Ltd., Great Britain.

EXAMPLE 6

Assays for the Examination of the Toxicity

Due to the given structure of the substances and the fact that today the toxicity of the newly developed substances is examined already at an early stage of the target identification, examinations of the toxicity were performed in different cell types using different test kits.

1) XTT-Assay for the Examination of the Cellular Proliferation

The XTT-assay (Cell Proliferation Kit II (XTT), Roche molekulare Biochemikalien, Mannheim, Germany) was used for the quantification of the anti-proliferative or cytotoxic effects of the substances as synthesized. The assay is based on the conversion of the yellow tetrazolium-salt XTT into an orange formazan-dye by metabolically active cells. The XTT-formazan-dye is soluble in aqueous solutions, and can be directly determined in a quantitative fashion with an ELISA-reader. The incubation time varies depending from the respective experimental setting (e.g. the kind of cell and the cellular concentrations used). Following the addition of the final XTT-reagent, the absorption was determined at 490 nm, at different points in time (e.g. 30 minutes, 4, 6, 8, 12, and 18 hours). All data were analyzed with Microsoft Excel. The $IC_{50}$ values were calculated with the program GRAFIT, Erithacus Software Ltd., Great Britain.

Figure 3:
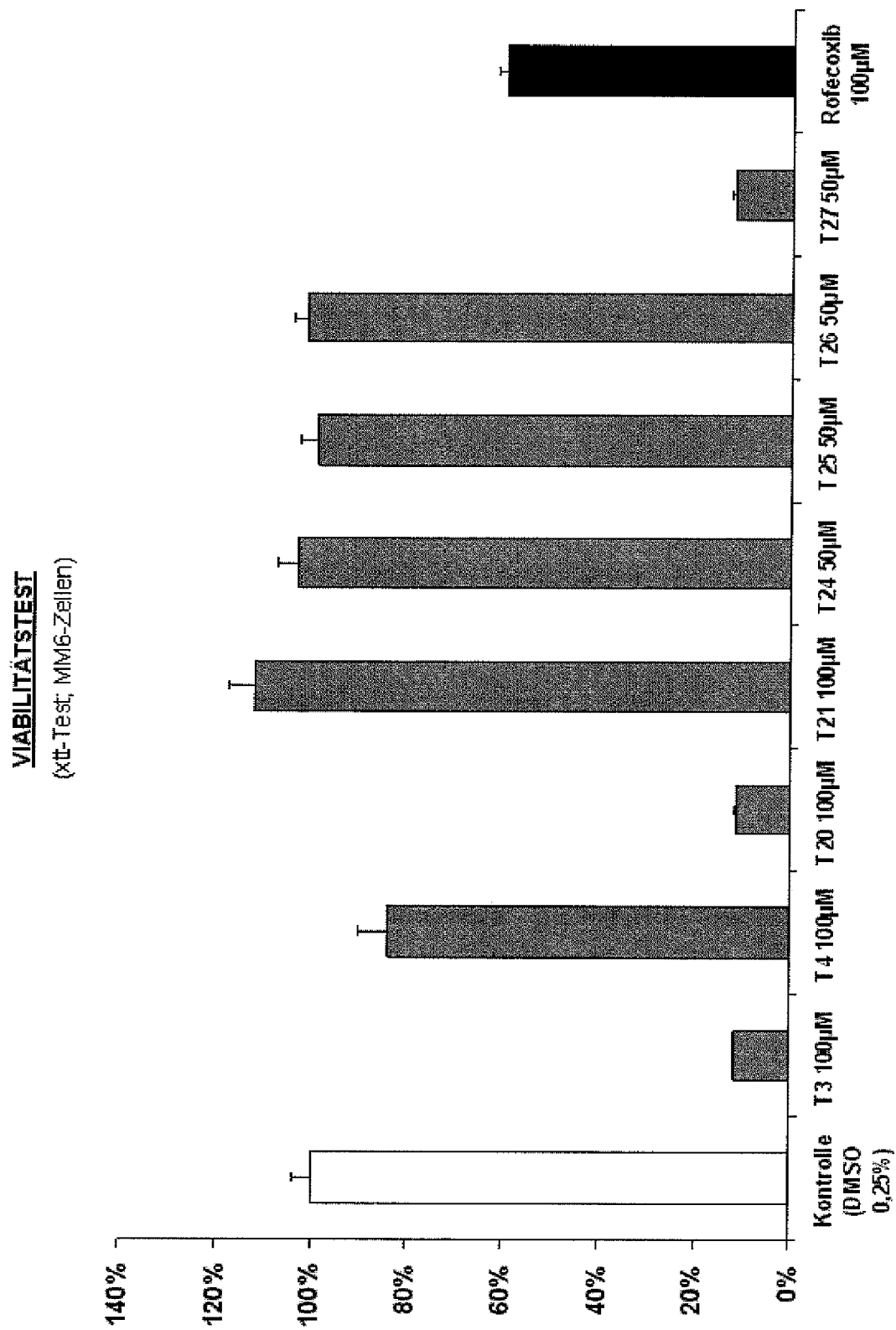

Results of the XTT-Viability Tests (FIG. 3)

Using the commercial available XTT-test kit, the cytotoxic behavior of substances with different structural elements against MM6-cells was examined after 1.5 hours. Structural elements that are responsible for the cytotoxicity were identified. The amide-function in combination with free carboxylic acid-functions was identified as particularly cytotoxic. By reducing the amide-function of T3 while maintaining of all other structural elements, a completely non-toxic but highly potent compound T21 (FIG. 4) is achieved. Nevertheless, it has to be kept in mind that Rofecoxib, which is already established on the market, has cytotoxic effects.

2) ATP-Lite-Assay

ATPLite™ (ATPLite™, Perkin Elmer Life Sciences, Boston Mass., USA) is a monitoring test of adenosine-triphosphate (ATP), which is based on the luciferase of the firefly (*Photinus pyralis*). This luminescence assay was developed for the quantitative evaluation of the proliferation and cytotoxicity of cultivated mammalian cells. The ATP-monitoring can be employed in order to examine the cytostatic and proliferative effects of different substances. The testing was performed in accordance with the instructions of the manufacturer.

EXAMPLE 7

Proteose-Peptone-Induced Peritonitis in Mice

Nine mice (three in each group) were anesthetized. Then, three mice each received the substance to be tested dissolved in 100 μl corn oil, 100 μl corn oil alone or HBSS, injected i.p. After 1 hour, each mouse received 3 ml of a 3% proteose-peptone-solution in HBSS, injected i.p. After 6 hours, the animals were sacrificed, and the leukocytes were collected using 3 ml cold HBSS containing 5 mM EDTA. The samples were centrifuged (2000 rpm for 5 minutes), and incubated with 5 μl FITC-conjugated rat-anti-mouse macrophage/monocyte antibody (MOMA-2, ImmunoKontact), anti-mouse PMN antibody (anti-PMN, ImmunoKontact), and anti-mouse T-lymphocyte antibody (anti-CD2, ImmunoKontact) for 20 minutes at 4° C. Then, a twofold washing and resuspension in HBSS took place. The intensity of the fluorescence of the leukocytes was analyzed by means of FACS.

Figure 2:
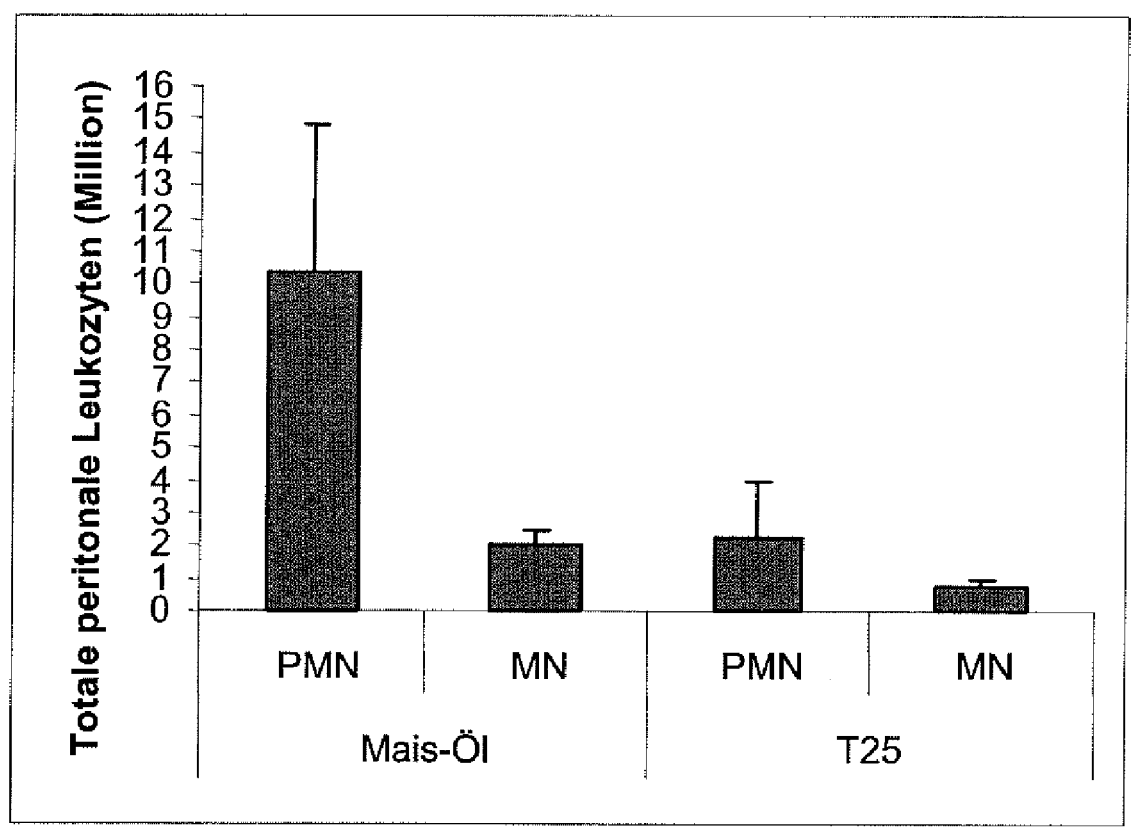
FIG. 2 shows the reduction of the polymorphonuclear leukocytes (PMNs)-infiltration by T25 in a mouse-peritonitis-model.

The results with compound T25 are depicted in FIG. 2, and, as an example, show that the compounds according to the invention led to a reduction of the PMN-infiltration into the peritoneum, and, thus, are anti-inflammatory effective.

EXAMPLE 8

General Instructions for Synthesis

In order to synthesize the dicarboxylic acid 1 (scheme 1), in a first reaction step 4-iodobenzoic acid methylester 3 is reacted with i-PrMgCl at low temperatures of below −20° C. (scheme 1). Thereby, a halogen-magnesium-exchange reaction occurs ((a) Jensen, A. E.; Dohle, W.; Sapountzis, I.; Lindsay, D. M.; Vu V. A.; Knochel P. *Synthesis* 2002, 565-569. (b) Boudier, A.; Bromm, L. O.; Lotz, M.; Knochel, P. *Angew. Chem. Int. Ed.* 2000, 39, 4414-4435. (c) Knochel, P.; Dohle, W.; Gommermann, N.; Kneisel, F. F.; Knopp, F.; Korn, T.; Sapountzis, I.; Anh Vu, V. *Angew. Chem. Int. Ed.* 2003, 42, 4302-4320.), whereby the Grignard-intermediate 4 is selectively formed in the presence of the methylester function. The subsequent reaction with 4-formylbenzoic acid methylester (16) finally provides the desired benzyl alcohol 5 in a yield of 71%. This is then oxidized to the corresponding benzophenone-derivative 6 with pyridiniumchlorochromate (PCC), and is subsequently converted into the oxime 7 in a yield of 80% in two steps through a reaction with hydroxylamine hydrochloride in the presence of sodium acetate in ethanol. The phloroglucine-fragment 10 as required for the following reaction step, is produced in two steps. For this, first, phloroglucine 8 is suspended in 1-decanol, and etherized through introduction of gaseous HCl into 9 (Bringmann, G.; Hartung, T.; Göbel, L.; Schupp, O.; Ewers, C. L. J.; Schöner, B.; Zagst, R.; Peters, K.; von Schnering, H. G.; Burschka, C. *Liebigs Ann. Chem.* 1992, 225-232.). In a second etherization step, compound 9 is then reacted with 1,6-dibromohexane, in order to produce the bromine compound 10 in a yield of 26% in two steps. In order to couple both fragments 7 and 10 one with the other, the oxime 7 is first deprotonated by sodium hydride in DMF, and subsequently reacted with the phloroglucine-component 10, and a catalytic amount of n-Bu$_4$NI at RT. The thus formed dimethylester 11 can be isolated in a yield of 91%. Through the effect of a 0.5 M aqueous sodium hydroxide solution in a mixture of ethanol and THF at RT 11 can be finally saponified to the desired dicarboxylic acid 1 in a yield of 95%. Therefore, 1 can be synthesized in five steps with an overall yield of 52%. In order to synthesize the dicarboxylic acid 2a (scheme 2), 4-iodobenzoic acid ethylester 12 is reacted with 4-acetamidobenzoic acid ethylester 13 in an Ullmann-reaction in accordance with the reaction conditions as described (Hellwinkel, D.; Gaa, H. G.; Gottfried, R. Z. *Naturforsch.* 1986, 41 b, 1045-1060.) to give 14. The effect of sodium methanolate in methanol leads to the formation of the respective methylester-functions with simultaneous leaving of the acetyl-group, in order to give the desired dimethylester 15a in a yield of 81%. In the next reaction step, compound 15a is then first deprotonated using sodium hydride in n-Bu$_2$O, and is subsequently reacted with 6-bromohexanic acid chloride, delivering compound 19a in a yield of 88% (SØrensen, J. L.; Huusfeldt, P. O.; Knutsen, L. J. S.; Lau, J.; Lundt, B. F.; Petersen, H.; Suzdak, P. D.; Swedberg M. D. B. *J. Med. Chem.* 1999, 42, 4281-4291.). If 19a is heated together with the phloroglucine-derivative 10 in the presence of potassium carbonate and a catalytic amount of potassium iodide in cyclohexanone, the coupling into the dimethylester 20a can be achieved in a yield of 66%. In the last step of the synthesis, the ester functions in 20a are saponified by stirring with a 0.5 M solution of LiOH in THF, in order to give the desired dicarboxylic acid 2a in a yield of 89%, or in an overall yield of 42% in four steps starting from 14, respectively.

The production of the dicarboxylic acid 2b (scheme 2) starts from the 4-formylbenzoic acid-methylester 16, as well as 4-aminobenzoic acid methylester 17, which in the first reaction step are condensated into the imine 18. Reduction of the double bond in 18 by the effect of NaBH$_4$ in MeOH at RT gives the amine 15b in a yield of 82% via two steps (scheme 2) (Albright, J. D.; DeVries, V. G; Largis, E. E.; Miner, T. G.; Reich, M, F.; Schaffer, S. A.; Shepherd, R. G.; Upeslacis, J. *J. Med. Chem.* 1983, 26, 1378-1393). The further synthesis steps are performed in analogy to the already described synthesis of the dicarboxylic acid 2a. Then, the compound 15b is deprotonated with sodium hydride, and subsequently converted into the amide 19b through the addition of 6-dibromohexanoic acid (yield of 91%). The subsequent reaction with the phloroglucine-component 9 delivers the coupling product 20b in a yield of 85%. The saponification of the dimethylester 20b with a solution of 0.5 M LiOH in THF finally gives the desired dicarboxylic acid 2b in a yield of 80% and an overall yield of 51% in five steps starting from 16.

EXAMPLE 9

General Method for Synthesis

Melting points are indicated without correction, and were determined with an apparatus according to Dr. Tottoli of the company Büchi. Infrared spectra were recorded on the apparatus PerkinElmer 1310 Infrared Spectrometer. $^1$H-NMR-spectra were measured on the apparatus AC 300 of the company Bruker. Chemical shifts are indicated relative to tetramethylsilane as internal standard. Mass spectra were measured with the apparatuses MAT 95 (FD, 70 eV) of the company Finnigan or MAT 311 A (EI, 70 eV) of the company Varian. Elementary analyses were performed with the apparatus Carlo Erba Strumentazione 1106 at the Institut für Organische Chemie of the Johannes Gutenberg-Universität in Mainz. The values as identified are found within a deviation of ±0.4%. The sequence of the reactions, as well as the purity of the products were checked by means of thin layer chromatography using the stationary phase silica gel 60 F$_{254}$ (0.2 mm coated plates) of the company Merck. Column chromatography was performed on silica gel with a size of the beads of 60-200 Mm from the company J. T. Baker. The solvents and reagents as used were purified and dried according to standard laboratory method, if required, or used as obtained from the respective company. Reactions in anhydrous solvents were performed under dry nitrogen as a standard. Compound 14 was produced according to the method as described in Hellwinkel et al. (Hellwinkel, D.; Gaa, H. G.; Gottfried, R. Z. *Naturforsch.* 1986, 41 b, 1045-1060.).

EXAMPLE 10

Specific Instructions for Syntheses

1) Bis(4-methoxycarbonylphenyl)methanol (5)

(Andersen, K. E.; Mane, R. B.; Desai, U. V.; Hebbalkar, G. D. *Collection Czechoslovak Chem. Commun.* 1988, 53, 646-657.) 4-Iodobenzoic acid 3 (5.00 g, 19.1 mmol) is dissolved in anhydrous THF (60 ml), the solution is cooled to an internal temperature of −30° C. in a bath of iso-propanol/dry-ice, and i-PrMgCl (2 M in THF; 10.5 ml, 21.0 mmol) is slowly added dropwise, in order to keep the internal temperature at between −20° C. and −30° C. After the reaction mixture is stirred for an additional 40 min at a temperature of −25° C., a solution of 4-formylbenzoic acid methylester (16; 4.07 g, 24.8 mmol) in anhydrous THF (25 ml) is added dropwise, in order to keep the internal temperature at below −20° C. The mixture is stirred for an additional 30 min at −25° C. and is thawed over night to RT. Subsequently, methanol (30 ml) is added, the mixture is poured into water (500 ml), and extracted with Et$_2$O. The organic phases are unified, washed with a saturated solution of NaCl, and dried over MgSO$_4$. The solvent is removed, and the crude product as obtained is crystallized from chloroform/petroleum ether, in order to obtain 4.05 g (71%) of compound 5 as a colorless solid. Melting point 116° C. (Andersen, K. E.; Mane, R. B.; Desai, U. V.; Hebbalkar, G. D. *Collection Czechoslovak Chem. Commun.* 1988, 53, 646-657.) 123° C.). The spectroscopic data of the isolated compound 5 correspond to the values as published (Andersen et al. 1988, see above).

2) Bis(4-methoxycarbonylphenyl)methanone (6)

(Kirste, B.; Grimm, M.; Kurreck, H. *J. Am. Chem. Soc.* 1989, 111, 108-114.) To a suspension of PCC (3.10 g, 14.4 mmol) in anhydrous CH$_2$Cl$_2$ (25 ml) at RT, a solution of the benzyl alcohol 5 (2.70 g, 8.99 mmol) is added slowly dropwise into anhydrous CH$_2$Cl$_2$ (10 ml), and the preparation is stirred at this temperature over night. Subsequently, the mixture is filtered through a small amount of silica gel (CH$_2$Cl$_2$ as eluent). Following the distillation of the solvent, 2.44 g (91%) of compound 6 could be isolated in form of a colorless solid. Melting point 228-230° C. (Kirste et al. 1989, see above, 229.5-230° C.); IR (KBr) 1705, 1630 cm$^{-1}$; $^1$H-NMR (CDCl$_3$) δ 8.17 (d, 8.4 Hz, 4H), 7.85 (d, 8.4 Hz, 4H), 3.98 (s, 6H); MS (EI) m/z 298 (M$^+$). Anal. calc. for C$_{17}$H$_{14}$O$_5$: C, 68.45; H, 4.73. Found C, 68.30; H, 4.69.

3) Bis(4-methoxycarbonylphenyl)methanone-oxime (7)

A mixture of 6 (2.33 g, 7.81 mmol), HCl-H$_2$NOH (1.63 g, 23.4 mmol) and sodium acetate (1.92 g, 23.4 mmol) in Ethanol (80 ml) was heated for 24 h under reflux. The mixture was allowed to cool to RT, and half concentrated NaHCO$_3$-solution (200 ml) was added. The aqueous phase was extracted with Et$_2$O, the unified organic phases were washed with saturated solutions of NaHCO$_3$ and NaCl, and dried over Na$_2$SO$_4$. The solvent was removed, and the crude product is crystallized from ethanol. 2.15 g (88%) of compound 7 are obtained as a colorless solid. Melting point 177-178° C.; IR (KBr) 3190, 2920, 1700, 1585 cm$^{-1}$; $^1$H-NMR (CDCl$_3$) δ 8.50 (s$_{br}$, 1H), 8.16 (d, 8.6 Hz, 2H), 8.00 (d, 8.6 Hz, 2H), 7.51 (d, 8.6 Hz, 2H), 7.47 (d, 8.6 Hz, 2H), 3.96 (s, 3H), 3.93 (s, 3H); MS (EI) m/z 313 (M$^+$). Anal. calc. for C$_{17}$H$_{15}$NO$_5$: C, 65.17; H, 4.83; N, 4.47. Found C, 65.14; H, 4.78; N, 4.47.

4) 3,5-didecyloxyphenol (9)

Into a suspension of phloroglucin 8 (5.00 g, 39.7 mmol) in 1-decanol (80 ml) dry gaseous HCl is introduced for 40 min, and the orange/red mixture is subsequently heated to 70° C. for an additional 3.5 h. After finalization of the reaction, the excess 1-decanol is distilled off in vacuo, and the residue of the reaction is purified by means of column chromatography (silica gel, CH$_2$Cl$_2$). 5.92 g (37%) of compound 9 are obtained as a colorless solid. Melting point: 48-50° C.; IR (KBr) 3340, 2880, 2810 cm$^{-1}$; $^1$H-NMR (CDCl$_3$) δ 6.06 (t, 2.1 Hz, 1H), 5.99 (d, 2.1 Hz, 2H), 4.80 (s, 1H, OH), 3.89 (t, 6.7 Hz, 4H), 1.80-1.69 (m, 4H), 1.48-1.23 (m, 28H), 0.88 (t, 6.8 Hz, 6H); MS (FD) m/z 407 (M$^+$). Anal. calc. for C$_{26}$H$_{46}$O$_3$. C, 76.79; H, 11.40. Found C, 76.74; H, 11.44.

5) 1-(6-Bromohexyloxy)-3,5-didecyloxybenzene (10)

A mixture of 9 (2.70 g, 6.64 mmol), 1,6-dibromohexane (15.0 ml, 98.4 mmol), K$_2$CO$_3$ (2.29 g, 16.6 mmol) in cyclohexanone (50 ml) was heated for 16 h under reflux. The mixture was allowed to cool to RT, the inorganic salts are filtered off, followed by rinsing with acetone. The solvent and the excess 1,6-dibromohexan are distilled off in vacuo, and the residue is purified by means of column chromatography (silica gel, chloroform/petroleum ether 1:2). 2.62 g (69%) of compound 10 could be isolated in form of a light yellow oil. IR (film) 2895, 2810, 1575 cm$^{-1}$; $^1$H-NMR (CDCl$_3$) δ 6.05 (s, 3H), 3.94-3.86 superimposed signals (3.91, t, 6.4 Hz, 2H and 3.90, t, 6.7 Hz, 4H), 3.42 (t, 6.7 Hz, 2H), 1.95-1.83 (m, 2H), 1.81-1.69 (m, 6H), 1.52-1.21 (m, 32H), 0.88 (t, 6.8 Hz, 6H); MS (FD) m/z 571 (M$^+$ for Br$^{81}$), 569 (M$^+$ for Br$^{79}$). Anal. calc. for C$_{32}$H$_{57}$BrO$_3$: C, 67.46; H, 10.08. Found C, 67.67; H, 10.12.

6) O-[6-(3,5-Didecyloxyphenyloxy)-hexyl]-bis(4-methoxycarbonylphenyl)methanone-oxime (11)

Into a suspension of sodium hydride (60% in mineral oil; 140 mg, 3.51 mmol) in anhydrous DMF (5 ml) the oxime 7 (1.00 g, 3.19 mmol) is added batch wise at 0° C., and stirred for an additional 15 min. Then, a solution of the bromide 10 (1.81 g, 3.19 mmol) in anhydrous DMF (3 ml), and a catalytic amount of n-Bu$_4$NI are added to the intensively red reaction mixture. After stirring for one hour at RT (DC-control), the reaction is poured into water, and extracted with Et$_2$O. The unified organic phases are washed with water and saturated NaCl-solution, and dried over Na$_2$SO$_4$. After removal of the solvent, the residue is purified through column chromatography on silica gel (ethyl acetate/petroleum ether 1:4). 2.81 g (91%) of compound 11 are obtained as a colorless solid. Melting point. 55-56° C.; IR (KBr) 2890, 2820, 1705, 1580 cm$^{-1}$; $^1$H-NMR (CDCl$_3$) δ 8.11 (d, 8.4 Hz, 2H), 7.99 (d, 8.4 Hz, 2H), 7.52 (d, 8.4 Hz, 2H), 7.40 (d, 8.4 Hz, 2H), 6.05 (s, 3H), 4.22 (t, 6.7 Hz, 2H), 3.95 (s, 3H), 3.92 (s, 3H), 3.89 (t, 6.7 Hz, 6H), 1.80-1.67 (m, 8H), 1.49-1.21 (m, 32H), 0.88 (t, 6.8 Hz, 6H); MS (FD) m/z 802 (M$^+$). Anal. calc. for C$_{49}$H$_{71}$NO$_8$: C, 73.37; H, 8.92; N, 1.75. Found C, 73.87; H, 8.67; N, 1.74.

7) O-[6-(3,5-Didecyloxyphenyloxy)-hexyl]-bis(4-carboxyphenyl)methanone-oxime (1)

The diethyl ester 11 (500 mg, 0.623 mmol) is dissolved in a mixture of ethanol (5.10 ml) and THF (12.3 ml) and is stirred at RT for 24 h with an aqueous NaOH-solution (0.5 M, 3.75 ml). After finalization of the reaction water (30 ml) is added, and extracted once with Et$_2$O (for phase separation, the mixture is drained into an Erlenmeyer flask, and put for about 24h into a fridge). Then, the clear aqueous phase is separated off, and the organic phase, together with the residual mix-phase, is discarded. A 1 M solution of hydrochloric acid is added slowly and dropwise to the aqueous phase until a pH-value of 6-5 is obtained. It is extracted with Et$_2$O, the organic phases are unified, washed with water and saturated NaCl-solution, and dried over Na$_2$SO$_4$. After removal of the solvents 458 mg (95%) of compound 1 are isolated as a colorless resin. IR (KBr) 3250, 2890, 2820, 2640, 2520, 1670, 1580 cm$^{-1}$; $^1$H-NMR (CDCl$_3$) δ 8.21 (d, 8.4 Hz, 2H), 8.09 (d, 8.4 Hz, 2H), 7.58 (d, 8.4 Hz, 2H), 7.45

(d, 8.4 Hz, 2H), 6.05 (s, 3H), 4.24 (t, 6.4 Hz, 2H), 3.89 (t, 6.4 Hz, 6H), 1.81-1.68 (m, 8H), 1.51-1.22 (m, 32H), 0.87 (t, 6.7 Hz, 6H); MS (FD) m/z 774 (M$^+$). Anal. calc. for $C_{47}H_{67}NO_8$: C, 72.93; H, 8.72; N, 1.81. Found C, 72.47; H, 8.96; N, 1.79.

8) N,N-bis(4-methoxycarbonylphenyl)amine (15a)

After dissolving sodium (971 mg, 42.2 mmol) in anhydrous methanol (75 ml), compound 14 (Walter, R. I. *J. Am. Chem. Soc.* 1955, 77, 5999-6002.) (5.00 g, 14.1 mmol) is added batch wise, and the resulting reaction mixture is heated for 1.5 h under reflux. The mixture is then allowed to cool to RT, and the preparation is poured on ice. The solid as formed is aspirated, and crystallized from methanol, in order to precipitate 3.25 g (81%) of compound 15a as colorless needles. Melting point 174-175° C. (Walter et al. 1955, see above, 177-178° C.); IR (KBr) 3280, 3260, 2920, 1695, 1665, 1570 cm$^{-1}$; $^1$H-NMR (CDCl$_3$) δ 7.98 (d, 8.8 Hz, 4H), 7.14 (d, 8.8 Hz, 4H), 6.42 (s$_{br}$, 1H, NH), 3.90 (s, 6H); MS (EI) m/z 285 (M$^+$). Anal. calc. for $C_{16}H_{15}NO_4$: C, 67.36; H, 5.30; N, 4.91. Found C, 67.42; H, 5.09; N, 4.97.

9) 6-bromohexanoic acid-N,N-bis(4-methoxycarbonylphenyl)amide (19a)

To a suspension of sodium hydride (60% in mineral oil; 77.1 mg, 1.93 mmol) in anhydrous n-Bu$_2$O (5 ml) 15a (500 mg, 1.75 mmol) is added batch wise, and the mixture is stirred for an additional two hours at RT. Then, 6-bromohexanoic acid chloride (0.314 ml, 2.10 mmol) is added, and the reaction is heated for 4 h under reflux. The mixture is allowed to cool to RT, poured into ice-water, and extracted with CH$_2$Cl$_2$. The organic phases are unified, washed with a saturated solution of NaHCO$_3$ (2×) and saturated NaCl, and dried over MgSO$_4$. Finally, the solvent is distilled off, and the crude product is crystallized from methanol. 713 mg (88%) of the desired compound 19a are obtained as a colorless solid. Melting point. 133-135° C.; IR (KBr) 2920, 1700, 1645, 1580 cm$^{-1}$; $^1$H-NMR (CDCl$_3$) δ 8.06 (d, 8.6 Hz, 4H), 7.30 (d, 8.6 Hz, 4H), 3.92 (s, 6H), 3.38 (t, 6.7 Hz, 2H), 2.29 (t, 7.4 Hz, 2H), 1.88-1.77 (m, 2H), 1.76-1.64 (m, 2H), 1.49-1.35 (m, 2H); MS (FD) m/z 464 (M$^+$+1 for Br$^{81}$), 462 (M$^+$+1 for Br$^{79}$).

10) 6-(3,5-Didecyloxyphenoxy)-hexanoic acid-NA-bis(4-methoxycarbonylphenyl)amide (20a)

A mixture of 19a (600 mg, 1.30 mmol), Phenol 9 (528 mg, 1.30 mmol), K$_2$CO$_3$ (449 mg, 3.25 mmol) and a catalytic amount of KI in cyclohexanone (9 ml) are refluxed for 5 h. The mixture is allowed to cool to RT, filtered off from the inorganic salts, followed by rinsing with acetone, and the solvent is largely distilled off. Finally, the residue as obtained is purified through column chromatography an silica gel (ethyl acetate/petroleum ether 1:2), in order to isolate 673 mg (66%) of compound 20a as a colorless solid. Melting point. 58-59° C.; IR (KBr) 2890, 2820, 1705, 1665, 1585 cm$^{-1}$; $^1$H-NMR (CDCl$_3$) δ 8.05 (d, 8.6 Hz, 4H), 7.29 (d, 8.6 Hz, 4H), 6.05 (t, 2.1 Hz, 1H), 6.02 (d, 2.1 Hz, 2H), 3.92 (s, 6H), 3.91-3.84 (m, 6H), 2.29 (t, 7.4 Hz, 2H), 1.80-1.66 (m, 8H), 1.52-1.21 (m, 30H), 0.88 (t, 6.7 Hz, 6H); MS (FD) m/z 788 (M$^+$). Anal. calc. for $C_{48}H_{69}NO_8$: C, 73.16; H, 8.83; N, 1.78. Found C, 72.90; H, 8.82; N, 1.72.

11) 6-(3,5-Didecyloxyphenoxy)-hexanoic acid-N,N-bis(4-carboxyphenyl)amide (2a)

The dimethylester 20a (500 mg, 0.635 mmol) is dissolved in THF (16 ml), and the stirred with an aqueous LiOH-solution (0.5 M, 3.81 ml, 1.90 mmol) for 8 h at 5° C., and for 16 h at 15° C. After finalization of the saponification (DC-control), water (50 ml) is added, and the mixture is extracted once with Et$_2$O. This mixture is drained into an Erlenmeyer flask, and the separation of the phases is awaited over night in a fridge. The ether phase and the mix-phase are discarded. The clear aqueous phase is brought to pH I by the slow and dropwise addition of a 1.0 M solution of hydrochloric acid. After extraction with Et$_2$O, the organic phases are unified, washed with water and saturated NaCl-solution, and dried over MgSO$_4$. The solvent is distilled off, and the resulting crude product is crystallized from methanol. 428 mg (89%) of compound 2a were isolated as a colorless solid. Melting point. 158-160° C.; IR (KBr) 3030, 2890, 2820, 2640, 2520, 1660, 1580 cm$^{-1}$; $^1$H-NMR (CDCl$_3$) δ 8.13 (d, 8.6 Hz, 4H), 7.33 (d, 8.6 Hz, 4H), 6.06 (t, 2.1 Hz, 1H), 6.03 (d, 2.1 Hz, 2H), 3.88 (d, 6.4 Hz, 6H), 2.33 (t, 7.2 Hz, 2H), 1.81-1.67 (m, 8H), 1.51-1.21 (m, 30H), 0.87 (t, 6.7 Hz, 6H); MS (FD) m/z 760 (M$^+$). Anal. calc. for $C_{46}H_{65}NO_8$: C, 72.70; H, 8.62; N, 1.84. Found C, 72.68; H, 8.61; N, 1.84.

12) N-(4-carboxybenzyl)-N-(4-carboxyphenyl)amine (15b)

A mixture of 4-formylbenzoic acid methylester 16 (2.00 g, 12.2 mmol), 4-aminobenzoic acid methylester 17 (1.84 g, 12.2 mmol) in anhydrous MeOH (20 ml) is heated for 1 h under reflux. The reaction is allowed to cool to RT, the solid as formed is aspirated, followed by rinsing with MeOH, and the product is finally dried under high vacuum. 3.41 g of compound 18 (94%) were isolated as a colorless solid. The product was used directly in the following reaction, and without further spectroscopic characterization.

To a suspension of imine 18 (3.41 g, 11.5 mmol) in anhydrous MeOH (107 ml) NaBH$_4$ (564 mg, 14.9 mmol) is added batch wise at RT, and the mixture is stirred for an additional 24 h at RT. Subsequently, the reaction mixture is poured into ice-water (200 ml), and extracted with Et$_2$O. The organic phases are unified, washed with water and saturated NaCl-solution, and dried over MgSO$_4$. Finally, the solvents are removed, and the crude product is crystallized from MeOH, in order to obtain 2.99 g (87%) of compound 15b as colorless needles. Melting point. 133-135° C.; IR (KBr) 3685, 2905, 1720, 1585 cm$^{-1}$; $^1$H-NMR (CDCl$_3$) δ 8.01 (d, 8.4 Hz, 2H), 7.85 (d, 8.8 Hz, 2H), 7.41 (d, 8.4 Hz, 2H), 6.57 (d, 8.8 Hz, 2H), 4.65 (s$_b$, 1H), 4.46 (s, 2H), 3.91 (s, 3H), 3.84 (s, 3H); MS (EI) m/z 299 (M$^+$). Anal. calc. for $C_{17}H_{17}NO_4$. C, 68.21; H, 5.72; N, 4.68. Found C, 68.42; H, 5.84; N, 4.64.

13) 6-bromohexanoic acid-N-(4-methoxycarbonylbenzyl)-N-(4-methoxycarbonylphenyl)-amide (19b)

Following the reaction instructions for the production of compound 19a, the amine 15b (856 mg, 2.86 mmol) is first added to a suspension of sodium hydride (60% in mineral oil; 126 mg, 3.15 mmol) in anhydrous n-Bu$_2$O (12 ml) and the resulting mixture is then added with 6-bromohexanoic acid chloride (0.51 ml, 3.43 mmol). The crude product that is obtained after processing is purified through column chromatography (silica gel, ethyl acetate/petroleum ether 1:2). 1.24 g (91%) of compound 19b are obtained as a colorless. Melting point. 190-191° C.; IR (Film) 2970, 2920, 2840, 1705, 1645, $1590 \text{ cm}^{-1}$; $^1$H-NMR (CDCl$_3$) δ 8.02 (d, 8.6 Hz, 2H), 7.94 (d, 8.4 Hz, 2H), 7.25 (d, 8.4 Hz, 2H), 7.05 (d, 8.4 Hz, 2H), 4.95 (s, 2H), 3.92 (s, 3H), 3.90 (s, 3H), 3.36 (t, 6.7 Hz, 2H), 2.11 (t, 7.4 Hz, 2H), 1.85-1.72 (m, 2H), 1.71-1.57 (m, 2H), 1.42-1.29 (m, 2H); MS (FD) m/z 477 (M$^+$ for Br$^{81}$), 475 (M$^+$ for Br$^{79}$).

14) 6-(3,5-Didecyloxyphenoxy)hexanoic acid-N-(4-methoxycarbonylbenzyl)-N-(4-methoxycarbonylphenyl)amide (20b)

A mixture of compound 19b (540 mg, 1.13 mmol), phenol 9 (461 mg, 1.13 mmol), K$_2$CO$_3$ (392 mg, 2.83 mmol), and a catalytic amount of KI in cyclohexanone (6.50 ml) is reacted in analogy to the already described reaction instructions for the synthesis of compound 20a. The subsequent purification through column chromatography (silica gel, ethyl acetate/petroleum ether 1:2) produced 768 mg (85%) of compound 20b as colorless oil. IR (film) 2900, 2830, 1710, 1650, 1590 cm$^{-1}$; $^1$H-NMR (CDCl$_3$) δ 8.00 (d, 8.6 Hz, 2H), 7.94 (d, 8.4 Hz, 2H), 7.25 (d, 8.4 Hz, 2H), 7.05 (d, 8.6 Hz, 2H), 6.05 (t, 1.9 Hz, 1H), 6.02 (d, 1.9 Hz, 2H), 4.95 (s, 2H), 3.92 (s, 3H), 3.91-3.82 superimposed signals (3.90, s, 3H and m, 6H), 2.12 (t, 7.4 Hz, 2H), 1.80-1.61 (m, 8H), 1.47-1.20 (m, 30H), 0.88 (t, 6.7 Hz, 6H); MS (FD) m/z 802 (M$^+$). Anal. calc. for C$_{49}$H$_{71}$NO$_8$: C, 73.37; H, 8.92; N, 1.75. Found C, 73.25; H, 8.78; N, 1.87.

15) 6-(3,5-Didecyloxyphenoxy)hexanoic acid-N-(4-carboxybenzyl)-N-(4-carboxyphenyl)-amide (2b).

Compound 20b (443 mg, 0.552 mmol) in THF (14 ml) is treated with an aqueous solution of LiOH (0.5 M, 3.31 ml, 1.66 mmol) in accordance with the production of compound 2a. 343 mg (80%) of the desired dicarboxylic acid 2b are obtained as a colorless resin. IR (KBr) 3030, 2890, 2820, 2640, 2520, 1700, 1655, 1575 cm$^{-1}$; $^1$H-NMR (CDCl$_3$) δ 8.08 (d, 8.6 Hz, 2H), 8.01 (d, 8.4 Hz, 2H), 7.29 (d, 8.4 Hz, 2H), 7.10 (d, 8.6 Hz, 2H), 6.05 (t, 1.9 Hz, 1H), 6.02 (d, 1.9 Hz, 2H), 5.01 (s, 2H), 3.92-3.83 (m, 6H) 2.16 (t, 7.4 Hz, 2H), 1.80-1.62 (m, 8H), 1.49-1.21 (m, 30H), 0.87 (t, 6.7 Hz, 6H); MS (FD) m/z (%) 774 (M$^+$). Anal. calc. for C$_{47}$H$_{67}$NO$_8$: C, 72.93; H, 8.72; N, 1.81. Found C, 72.65; H, 8.77; N, 1.77.

The invention claimed is:

1. A compound having the general formula 1

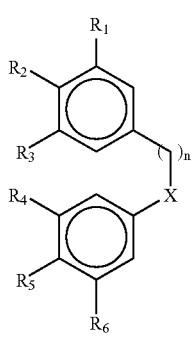

(1)

wherein n is 0 or 1,

R$_1$ to R$_6$ independently are H, COOH, COOCH$_3$, COOC$_2$H$_5$ or halogen, and X is C=N—O—(CH$_2$)$_m$—Y or N—C(=O)—(CH$_2$)$_m$—Y, wherein m is 5 or 6, and Y is

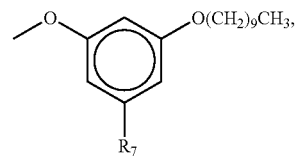

wherein

R$_7$ is H or O(CH$_2$)$_9$CH$_3$, or a derivative, diastereomer, or pharmaceutically acceptable salt thereof.

2. The compound according to claim 1, characterized in that the compound is formula 2,

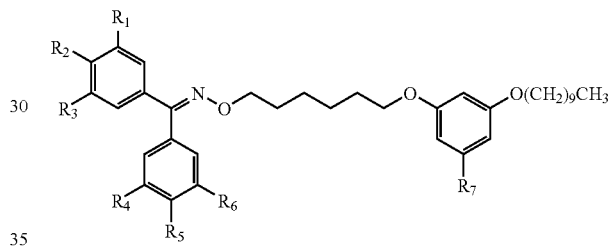

(2)

wherein

R$_1$ is H,

R$_2$ is H, COOH, COOCH$_3$ or halogen,

R$_3$ is H, COOH or COOCH$_3$,

R$_4$ is H,

R$_5$ is H, COOH, COOCH$_3$ or halogen,

R$_6$ is H, and

R$_7$ is H or O(CH$_2$)$_9$CH$_3$, or a derivative, diastereomer, or pharmaceutically acceptable salt thereof.

3. The compound according to claim 1, characterized in that the compound is formula 3,

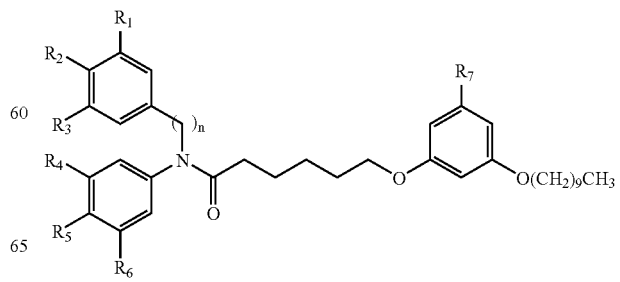

(3)

wherein
n is 0 or 1,
$R_1$ is H, COOH or COOCH$_3$,
$R_2$ is H, COOH, COOCH$_3$ or COOC$_2$H$_5$,
$R_3$ is H, COOH or COOCH$_3$,
$R_4$ is H, COOH or COOCH$_3$,
$R_5$ is H, COOH, COOCH$_3$ or COOC$_2$H$_5$,
$R_6$ is H, and
$R_7$ is H or O(CH$_2$)$_9$CH$_3$, or a derivative, diastereomer, or pharmaceutically acceptable salt thereof.

4. A pharmaceutical composition, comprising a compound having the general formula 1

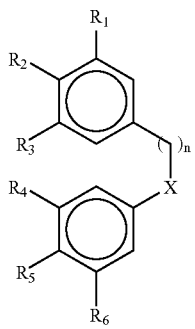
(1)

wherein
n is 0 or 1,
$R_1$ to $R_6$ independently are H, COOH, COOCH$_3$, COOC$_2$H$_5$ or halogen, and
X is C=N—O—(CH$_2$)$_m$—Y or N—C(=O)—(CH$_2$)$_m$—Y,
wherein
m is 5 or 6, and
Y is

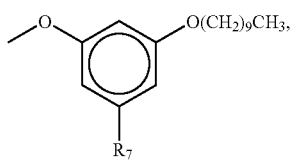

wherein
$R_7$ is H or O(CH$_2$)$_9$CH$_3$,
or a derivative, diastereomer, or, pharmaceutically acceptable salt thereof, and suitable additives or auxiliary agents.

5. The pharmaceutical composition according to claim 4, characterized in that the compound is present in form of a depot substance or as a precursor, together with a suitable, pharmaceutically acceptable diluent or carrier substance.

6. The pharmaceutical composition according to claim 4, characterized in that the compound is present in an amount of 0.1 to 1000 mg per dosage unit.

7. The pharmaceutical composition according to claim 4, characterized in that it contains additional selectin inhibitors.

8. The pharmaceutical composition according to claim 4 in the form of a tablet, dragee, capsule, droplet, suppository, formulation for injection or infusion for a peroral, rectal or parenteral use.

9. The pharmaceutical composition according to claim 4, characterized in that the compound is present in an amount in a concentration range of between 0.1 and 100 μM during the treatment in vivo.

10. A method for the treatment of a selectin-mediated disease wherein said treatment is the result of inhibiting selectin and wherein said method comprises administering, to a patient in need of such treatment, selectin-inhibiting a compound having the general formula 1

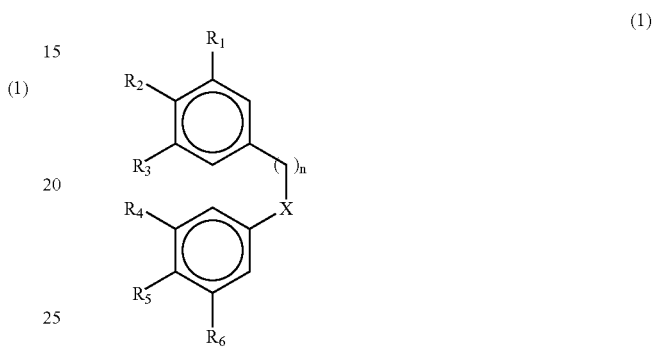
(1)

wherein
n is 0 or 1,
$R_1$ to $R_6$ independently are H, COOH, COOCH$_3$, COOC$_2$H$_5$ or halogen, and
X is C=N—O—(CH$_2$)$_m$—Y or N—C(=O)—(CH$_2$)$_m$—Y,
wherein
m is 5 or 6, and
Y is

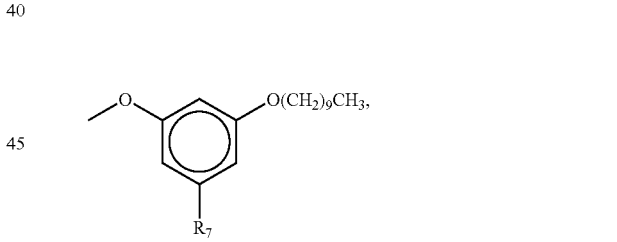

wherein
$R_7$ is H or O(CH$_2$)$_9$CH$_3$,
or a derivative, diastereomer, or pharmaceutically acceptable salt thereof.

11. The method according to claim 10 for the treatment of a disease wherein selectin-mediated leukocyte adhesion is dysregulated.

12. The method according to claim 10 for the treatment of an inflammatory disease or a tumorous disease.

13. The method according to claim 12, wherein the inflammatory disease is pertonitis or rheumatoid arthritis.

14. A method for selectin inhibition wherein said method comprises contacting a selectin with a compound having the general formula 1

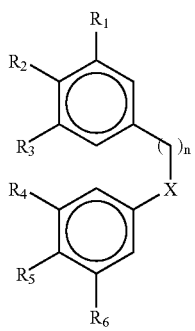

wherein n is 0 or 1.

$R_1$ to $R_6$ independently are H, COOH, COOCH$_3$, COOC$_2$H$_5$ or halogen, and X is C=N—O—(CH$_2$)$_m$—Y or N—C(=O)—(CH$_2$)$_m$—Y, wherein m is 5 or 6, and Y is

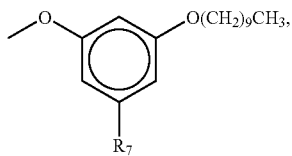

wherein $R_7$ is H or O(CH$_2$)$_9$CH$_3$, or a derivative, diastereomer, or pharmaceutically acceptable salt thereof.

15. A method for inhibiting the selectin-mediated adhesion of leukocytes by inhibiting selectin wherein said method comprises administering, to a patient in need of such inhibition, a selectin-inhibiting compound having the general formula 1

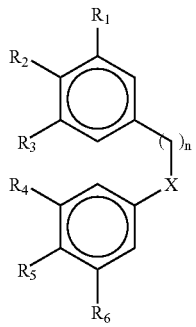

wherein n is 0 or 1, $R_1$ to $R_6$ independently are H, COOH, COOCH$_3$, COOC$_2$H$_5$ or halogen, and X is C=N—O—(CH$_2$)$_m$—Y or N—C(=O)—(CH$_2$)$_m$—Y, wherein m is 5 or 6, and Y is

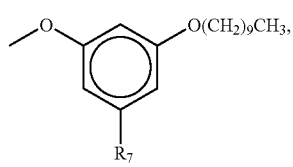

wherein $R_7$ is H or O(CH$_2$)$_9$CH$_3$, or a derivative, diastereomer, or pharmaceutically acceptable salt thereof.

* * * * *

UNITED STATES PATENT AND TRADEMARK OFFICE
CERTIFICATE OF CORRECTION

PATENT NO. : 7,485,742 B2
APPLICATION NO. : 11/572214
DATED : January 17, 2007
INVENTOR(S) : Dannhardt et al.

It is certified that error appears in the above-identified patent and that said Letters Patent is hereby corrected as shown below:

Column 2,
Line 7 "is able to bind to all three selecting, it" should read --is able to bind to all three selectins, it--.

Column 2,
Line 13 "E-selectin (Cooke, R.M., et al. The" should read --E-selectin (Cooke, R.M., et al., The--.

Column 3,
Line 31 "inhibitors of the selecting" should read --inhibitors of the selectins--.

Column 6,
Line 6 "N N-bis(4-" should read --N,N-bis(4- --.

Column 8,
Line 30 "(d) HC1.H$_2$N-" should read --(d) HC1·H$_2$N--.

Column 8,
Line 33 "n-BU4NI, 2" should read --n-Bu$_4$NI, 2--.

Column 13,
Line 5 "1) for the selecting," should read --1) for the selectins,--.

Column 16,
Line 9 "DM IRS-microscope" should read --DM IRB-microscope--.

Column 17,
Line 6 "DMSO (10-100 mM final" should read --DMSO (10-100 µM final--.

Column 20,
Lines 40-41 "the beads of 60-200 Mm" should read --the beads of 60-200 µm--.

UNITED STATES PATENT AND TRADEMARK OFFICE
CERTIFICATE OF CORRECTION

PATENT NO. : 7,485,742 B2
APPLICATION NO. : 11/572214
DATED : January 17, 2007
INVENTOR(S) : Dannhardt et al.

It is certified that error appears in the above-identified patent and that said Letters Patent is hereby corrected as shown below:

Column 23,
Line 48 "hexanoic acid-NA-bis" should read --hexanoic acid-N,N-bis--.

Column 28,
Lines 9-10 "treatment, selectin-inhibiting a compound" should read --treatment, a selectin-inhibiting compound--.

Signed and Sealed this

Second Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,485,742 B2
APPLICATION NO. : 11/572214
DATED : February 3, 2009
INVENTOR(S) : Dannhardt et al.

It is certified that error appears in the above-identified patent and that said Letters Patent is hereby corrected as shown below:

Column 2,
Line 7 "is able to bind to all three selecting, it" should read --is able to bind to all three selectins, it--.

Column 2,
Line 13 "E-selectin (Cooke, R.M., et al. The" should read --E-selectin (Cooke, R.M., et al., The--.

Column 3,
Line 31 "inhibitors of the selecting" should read --inhibitors of the selectins--.

Column 6,
Line 6 "N N-bis(4-" should read --N,N-bis(4- --.

Column 8,
Line 30 "(d) HC1.$H_2$N-" should read --(d) HC1·$H_2$N--.

Column 8,
Line 33 "n-BU4NI, 2" should read --n-$Bu_4$NI, 2--.

Column 13,
Line 5 "1) for the selecting," should read --1) for the selectins,--.

Column 16,
Line 9 "DM IRS-microscope" should read --DM IRB-microscope--.

Column 17,
Line 6 "DMSO (10-100 mM final" should read --DMSO (10-100 μM final--.

Column 20,
Lines 40-41 "the beads of 60-200 Mm" should read --the beads of 60-200 μm--.

UNITED STATES PATENT AND TRADEMARK OFFICE
CERTIFICATE OF CORRECTION

PATENT NO. : 7,485,742 B2
APPLICATION NO. : 11/572214
DATED : February 3, 2009
INVENTOR(S) : Dannhardt et al.

It is certified that error appears in the above-identified patent and that said Letters Patent is hereby corrected as shown below:

Column 23,
Line 48 "hexanoic acid-NA-bis" should read --hexanoic acid-N,N-bis--.

Column 28,
Lines 9-10 "treatment, selectin-inhibiting a compound" should read --treatment, a selectin-inhibiting compound--.

This certificate supersedes the Certificate of Correction issued June 2, 2009.

Signed and Sealed this

Twenty-third Day of June, 2009

JOHN DOLL
*Acting Director of the United States Patent and Trademark Office*